United States Patent
Stellas et al.

(10) Patent No.: US 10,287,294 B2
(45) Date of Patent: May 14, 2019

(54) COMPOUNDS FOR USE IN TREATING OR PREVENTING CANCEROUS DISEASES

(71) Applicant: BIOMEDICAL RESEARCH FOUNDATION OF THE ACADEMY OF ATHENS, Athens (GR)

(72) Inventors: Dimitris Stellas, Athens (GR); Constantin Tamvakopoulos, Athens (GR); Apostolos Klinakis, Iraklio (GR); Argiris Efstratiadis, Athens (GR); Zoe Cournia, Kifissia (GR)

(73) Assignee: BIOMEDICAL RESEARCH FOUNDATION OF THE ACADEMY OF ATHENS (GR)

( * ) Notice: Subject to any disclaimer, the term of this patent is extended or adjusted under 35 U.S.C. 154(b) by 0 days.

(21) Appl. No.: 15/742,330

(22) PCT Filed: Jul. 8, 2016

(86) PCT No.: PCT/EP2016/066340
§ 371 (c)(1),
(2) Date: Jan. 5, 2018

(87) PCT Pub. No.: WO2017/005919
PCT Pub. Date: Jan. 12, 2017

(65) Prior Publication Data
US 2018/0208597 A1 Jul. 26, 2018

(30) Foreign Application Priority Data

Jul. 8, 2015 (EP) .................................... 15175918

(51) Int. Cl.
| | |
|---|---|
| *C07D 487/04* | (2006.01) |
| *A61P 35/02* | (2006.01) |
| *A61K 31/635* | (2006.01) |
| *A61K 31/415* | (2006.01) |
| *A61K 31/4196* | (2006.01) |
| *A61K 31/519* | (2006.01) |
| *A61K 31/58* | (2006.01) |
| *A61K 31/7068* | (2006.01) |
| *A61K 31/196* | (2006.01) |
| *A61K 31/337* | (2006.01) |
| *A61K 31/365* | (2006.01) |
| *A61K 31/444* | (2006.01) |
| *A61K 31/517* | (2006.01) |
| *A61K 31/566* | (2006.01) |
| *A61K 31/704* | (2006.01) |
| *C07B 43/06* | (2006.01) |

(52) U.S. Cl.
CPC .......... *C07D 487/04* (2013.01); *A61K 31/415* (2013.01); *A61K 31/4196* (2013.01); *A61K 31/519* (2013.01); *A61K 31/58* (2013.01); *A61K 31/635* (2013.01); *A61K 31/7068* (2013.01); *A61P 35/02* (2018.01); *C07B 43/06* (2013.01); *A61K 31/196* (2013.01); *A61K 31/337* (2013.01); *A61K 31/365* (2013.01); *A61K 31/444* (2013.01); *A61K 31/517* (2013.01); *A61K 31/566* (2013.01); *A61K 31/704* (2013.01); *A61K 2300/00* (2013.01)

(58) Field of Classification Search
CPC ....... C07D 487/04; C07B 43/06; A61P 35/02; A61K 2300/00; A61K 31/51; A61K 31/196; A61K 31/337; A61K 31/365; A61K 31/444; A61K 31/517; A61K 31/566; A61K 31/635; A61K 31/704
See application file for complete search history.

(56) References Cited

PUBLICATIONS

Wolff, Manfred E., Burger's Medicinal Chemistry and Drug Discovery, Fifth Ed., vol. 1: Principles and Practice, John Wiley & Sons, 1995, 975. (Year: 1995).*
Banker, Gilbert S. et al., Modem Pharmaceutics, Marcel Dekker, New York, 1996. (Year: 1996).*
West, Anthony R., Solid State Chemistry and Its Applications, Wiley, New York, 1988, 358. (Year: 1988).*
Yap, et al., Small-molecule inhibitors of dimeric transcription factors: Antagonism of protein-protein and protein-DNA interactions, Med. Chem. Comm., vol. 3, No. 5, p. 541 (2012). (Year: 2012).*
Kiessling, et al., Selective Inhibition of c-Myc/Max Dimerization by a Pyrazolo[1,5-a]pyrimidine, Chem. Med. Chem., vol. 2, No. 5, 627-630 (2007). (Year: 2007).*
Kiessling et al., "Selective Inhibition of c-Myc/Max Dimerization by a Pyrazolo[1,5-a]pyrimidine," ChemMedChem 2(5):627-630 (2007).
Yap et al., "Small-molecule inhibitors of dimeric transcription factors: Antagonism of protein-protein and protein-DNA interactions," MedChemComm 3(5):541-551 (2012).

* cited by examiner

Primary Examiner — Erich A Leeser
(74) Attorney, Agent, or Firm — J.A. Lindeman & Co., PLLC

(57) ABSTRACT

The invention relates to new compounds of formula (I) that are useful in medicine, specifically in treating or preventing cancerous diseases in a mammal, to pharmaceutical compositions comprising such compounds, optionally together with other pharmaceutically active compounds, or to pharmaceutical formulations comprising such compounds or pharmaceutical compositions. The invention further relates to methods of making these compounds.

18 Claims, 5 Drawing Sheets
Specification includes a Sequence Listing.

a)

b)

SEQUENCE LISTING

```
<160> NUMBER OF SEQ ID NOS: 1

<210> SEQ ID NO 1
<211> LENGTH: 23
<212> TYPE: DNA
<213> ORGANISM: Artificial sequence
<220> FEATURE:
<223> OTHER INFORMATION: Human Myc2T binding oligonucleotide

<400> SEQUENCE: 1
tgggtgggtg gtttgttttt ggg                                            23
```

COMPOUNDS FOR USE IN TREATING OR PREVENTING CANCEROUS DISEASES

FIELD OF THE INVENTION

The invention relates to novel compounds that are useful in medicine, specifically in treating or preventing cancerous diseases in a mammal, and to pharmaceutical compositions comprising such compounds, optionally together with other pharmaceutically active compounds, as well as pharmaceutical formulations comprising such compounds or pharmaceutical compositions. The invention further discloses methods of making such compounds.

BACKGROUND OF THE INVENTION

Carcinogenesis is a process by which normal cells are transformed into cancer cells. It is characterized by a progression of changes at the cellular, genetic, and epigenetic level that ultimately reprogram a cell to undergo uncontrolled cell division, thus mostly forming a malignant mass. Though it is well-established that carcinogenesis is largely the result of irregular activation of oncogenes and/or inactivation of tumor-suppressors, which lead to various pathological changes, the reasons of carcinogenesis are various or not yet known. Furthermore, carcinogenesis pathways involve many genes, factors and conditions, which themselves and their interactions remain very complicated or unclear. Consequently, the development of anti-cancer drugs is simply based on the stroke of luck by trial-and-error, with the society still suffering under the lack of effective anti-cancer medications.

The Kras oncogene was first described in 1983 (McGrath J. P. et al., *Nature* 304, 501-506 (1983)) and thought to represent a potential drug target. For three decades, there have been many attempts to inhibit pharmacologically its carcinogenic action. Unfortunately, such efforts have so far failed (Watson J. *Open Biol* 3, 120144 (2013)). In parallel, Myc (formerly "c-Myc"), which acts downstream of Kras and other signaling pathways involved in carcinogenesis (such as Wnt and Notch), was also tested as a potential drug target for new anti-cancer drugs. Myc is functionally important for cellular proliferation, differentiation, apoptosis, and cell cycle progression and is found to be deregulated in many kinds of human tumors (Vita, M. & Henriksson, M. *Semin Cancer Biol* 16, 318-330 (2006)).

Myc along with Max belong to the basic helix-loop-helix leucin zipper (bHLHZip) protein family (Xu Y., et al., *Bioorg Med Chem* 14, 2660-2673 (2006)), and Myc can bind DNA only as a dimer with Max, whereby the complex formation activates the expression of many genes. A role of Myc in human cancers, for example, pancreatic ductal adenocarcinoma, was already suggested 20 years ago (Yamada H, et al., *Jpn J Cancer Res.* 77, 370-375 (1986)). Therefore, inhibition of Myc/Max dimerization has been studied in an attempt to control or modulate the progression of various cancers.

Until recently, Myc was not considered to be a suitable target for drug-treatment. Myc plays an essential role in the proliferation of all normal cells: The concern had been raised that systemic Myc inhibition would trigger devastating side effects, especially in the tissues exhibiting rapid turnover (Soucek, L., et al., *Nature* 455, 679-683 (2008)). However, experiments with "Omomyc", a mutant bHLHZip Myc domain of 90 amino acids, which acts in a dominant-negative fashion as a competitive inhibitor of Myc/Max dimerization-dependent transcription by forming a heterodimer with either Myc or Max have shown successful usage of inhibiting Myc/max interaction (Soucek, L., et al., loc. cit.). Systemic inhibition of Myc in mice carrying a conditionally activatable Omomyc construct resulted in mild and tolerable side-effects, while Omomyc action in the lung caused regression of LSL-Kras*-induced non-small-cell adenocarcinomas (Soucek, L., et al., loc. cit.).

Apart from the issue whether Myc represents a possible drug target, inhibition of Myc/Max dimerization has been the subject of research for quite some time, involving small peptides (D'Agnano, I. et al., *J Cell Physiol* 210, 72-80 (2007)), but also small molecules, which may exhibit an inhibitory effect on this dimerization. For example, Berg, T., et al., (*Proc Natl Acad Sci USA* 99, 3830-3835 (2002)) reported two small-molecule inhibitors of Myc/Max dimerization. Yin X., et al., reported another four compounds disrupting the association between Myc and Max (Yin X., *Oncogene* 22, 6151-6159, (2003)). Xu, Y, et al. reported yet another four compounds showing in vitro inhibitory effects on Myc/Max dimerization (Xu Y., et al., *Bioorg Med Chem* 14, 2660-2673 (2006)). Kiessling et al., further reported five test compounds including Mycro3, some of which exhibited selective Myc/Max dimerization (Kiessling, A., et al., *ChemMedChem* 2, 627-630 (2007)).

Although there are several in vitro studies on Myc/Max dimerization inhibitors, very few reported in vivo effects of those compounds. The compound 10058-F4 was among the first compounds found to be an inhibitor of Myc/Max dimerization. Gomez-Curet et al. (*J Pediatr Surg* 41, 207-211 (2006)) reported that 10058-F4 also decreased Myc mRNA levels in lymphoma cells, and inhibited the cell growth in a time- and dose-dependent manner. Huang et al. (*Exp Hematol* 34, 1480-1489 (2006)) reported that 10058-F4 induced apoptosis and differentiation in primary acute myeloid leukemia cell cultures. Lin et al. (*Anticancer Drugs*, 18, 161-70 (2007)) showed that 10058-F4 arrested hepatocellular carcinoma cells at G9/G1 phase of the cycle. Sampson et al. (*Cancer Res* 67, 9762-70 (2007)) reported that 10058-F4 also inhibited Myc protein expression in Burkitt lymphoma cells.

Based on many encouraging in vitro results for 10058-F4, Guo et al. (*Cancer Chemother Pharmacol* 63, 615-625 (2009)) investigated the preclinical pharmacology in mice bearing human prostate cancer xenografts. However, surprisingly, no significant inhibition of tumor growth in mice was observed after two weeks in vivo treatment with either 20 or 30 mg/kg 10058-F4. The lack of antitumor activity of 10058-F4 in vivo was assumed to be based on its poor pharmacokinetics. Accordingly, this shows the inherent difficulty of predicting in vivo outcome in an animal disease model based on any observed in vitro efficacy.

Hence, there is still a need in the art for efficient therapeutics that can prevent or inhibit tumor growth in mammals, in particular in humans.

SUMMARY OF THE INVENTION

The present invention generally refers to compounds having a pyrazolo-[1,5-α]-pyrimidine scaffold. In particular, one aspect of invention relates to a compound of formula (I)

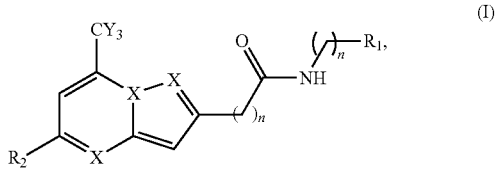

a tautomer, polymorph, hydrate, solvate, metabolite, prodrug, or a pharmaceutically acceptable salt thereof, wherein n is independently 0 or 1, preferably 1;
each X is independently C or N, preferably N;
Y is independently hydrogen, fluoro, chloro, or bromo; preferably fluoro or chloro;
$R_1$ and $R_2$, which may be the same or different, represent respectively

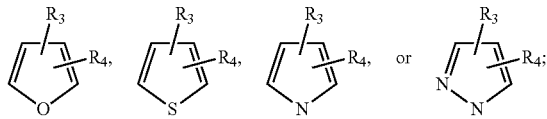

$R_3$ is a group —$R_5$—COOH (i.e. carboxyl) group or a pharmaceutically acceptable salt thereof; wherein $R_5$ is either a bond or a short $C_1$ to $C_3$-alkyl group; and $R_4$ is selected from any one of the following: substituted or unsubstituted ($C_5$-$C_{12}$) cycloalkyl or alkenyl, preferably a cyclohexyl, heterocyclic alkyl or mono- or dialkenyl, or substituted or unsubstituted ($C_5$-$C_{14}$) aryl, preferably a phenyl, or substituted or unsubstituted ($C_5$-$C_{10}$) heteroaryl.

In a preferred embodiment, formula (I) refers to a compound having the following formula (II):

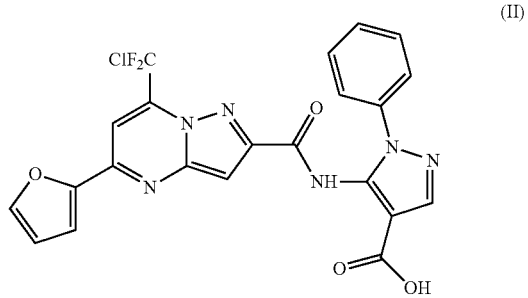

or a pharmaceutically acceptable salt thereof. This compound is also referred to herein with its internal name Amy22.

In another aspect, the invention further refers to a pharmaceutical composition comprising the compounds of formula (I) as defined above. Optionally, the pharmaceutical composition may further comprise one or more additional therapeutic agents, for example additional, otherwise known, anti-cancer agents.

The above pharmaceutical compositions may in certain embodiments further comprise one or more additional therapeutic agents, such as COX-2 oxygenase inhibitors.

In some embodiments, the pharmaceutical compositions may further comprise one or more agents inducing unscheduled DNA repair synthesis (UDS) at a target oncogene, preferably wherein the agent inducing unscheduled DNA repair synthesis (UDS) is a triple helix forming oligonucleotide specifically binding to Myc. Optionally, the compositions may further comprise one or more antimetabolites such as purine or pyrimidine analogs.

In another aspect of the invention, the compounds or the pharmaceutical compositions referred to herein are intended for use in medicine. Preferably, said compounds or pharmaceutical compositions are used in treating or preventing a cancerous disease in a mammal. Preferably, the mammal is human.

In some embodiments, the compounds or the pharmaceutical compositions are used in treating a cancerous disease that is susceptible to Myc overexpression and/or deregulation.

Another aspect of the invention relates to a method for the manufacture of the above compounds of formula (I):

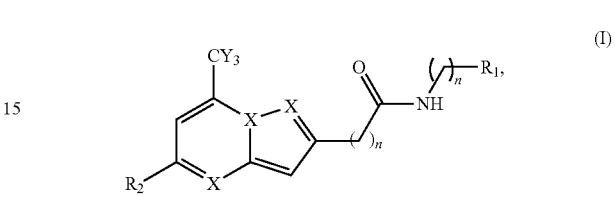

wherein the method comprises reacting a 2-carboxyl-substituted bicyclic moiety of formula (III):

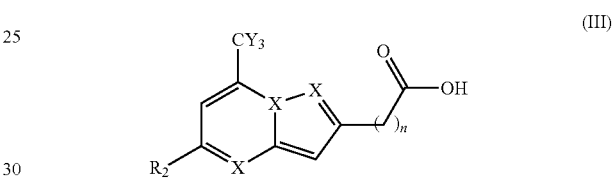

wherein X, $R_2$, $Y_3$ and n are defined as in claim 1, with a moiety $R_1$ as defined for formula (I) above but with an additional amino-group to form the corresponding amide compound of formula (I), to yield a compound of formula (II) as depicted above.

A: PET/CT of a mouse before and after treatment with Gemcitabine, as monotherapy (representative pictures from treated cohort). Shrinkage in tumor size and 18F-FDG uptake (dotted circles) is evident.

B: Histopathological features (H & E staining) of the treated tumor in (A). The analysis reveals the presence of scared fibrotic tissue and remnants of cancer cells. A few normal acini are also present.

C: PET/CT of a mouse before and after treatment with a combination of Gemcitabine and Amy22 (representative pictures from treated cohort). The diminished uptake of 18F-FDG by remnants of PDA is evident (compare the size of dotted circles).

D: Histopathological features (H & E staining) of the treated tumor in (C). The analysis reveals the presence of scared fibrotic tissue, remnants of cancer cells and a larger area consisting of normal acini.

E: Gamma counting of the exact overall 18F-FDG uptake post-mortem reveals that the remaining tumor after treatment with Gemcitabine alone is 31% of that of untreated PDA tumors (not shown; see Stellas et al., 2014). The corresponding percentage after the combination treatment is 18.6%.

We note that in some scans, there is high-level concentration of 18F-FDG in the urinary bladder (excretion of the tracer). High uptake of radioactivity (unrelated to the presence of tumor) is also noted in the heart.

Figure 6:
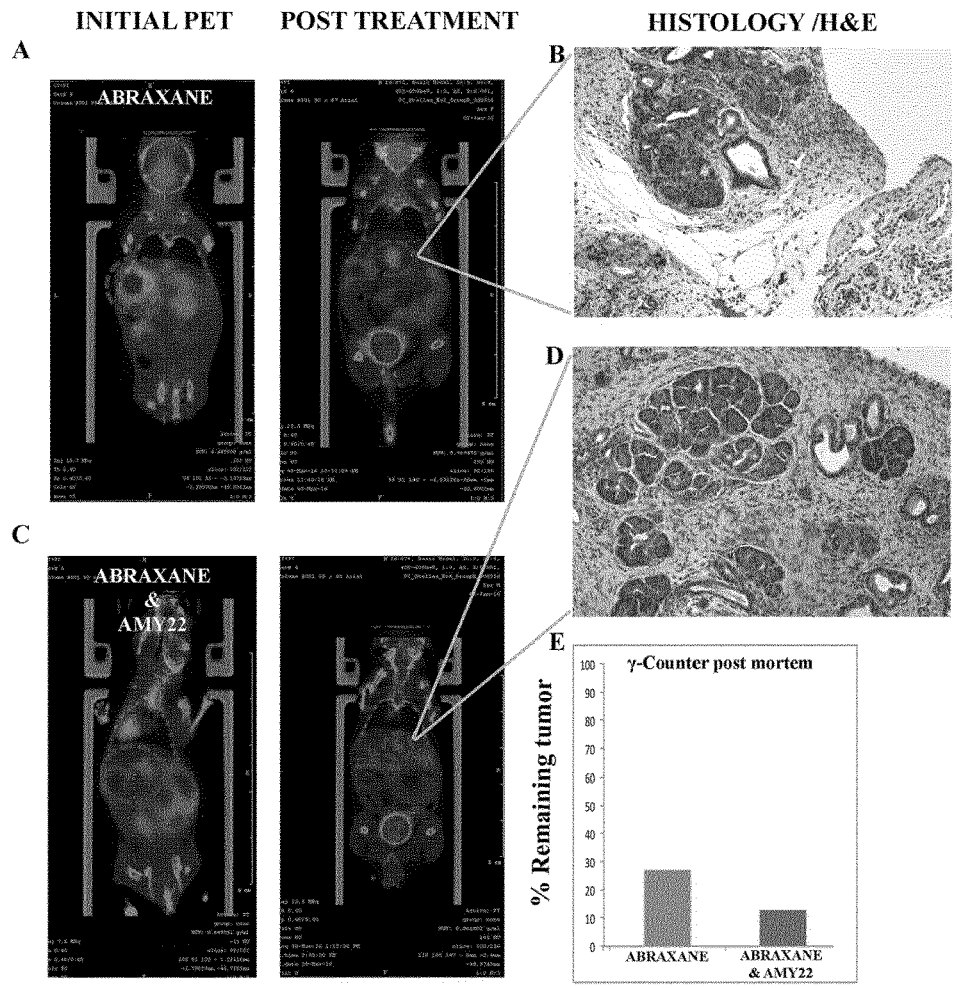

Conclusion: Amy22 enhances the efficacy of Gemcitabine that is classically used for human PDA chemotherapy FIG. 6: Example of micro PET/CT imaging of Pdx1-Cre/KRAS*A mouse at the beginning and end of treatment (one month) of pancreatic ductal adenocarcinoma (PDA) with Abraxane alone, or with Abraxane and Amy22.

A: PET/CT of a mouse before and after treatment with Abraxane, as monotherapy (representative pictures from treated cohort). Shrinkage in tumor size and 18F-FDG uptake (dotted circles) is evident.

B: Histopathological features (H & E staining) of the treated tumor in (A). The analysis reveals the presence of scared fibrotic tissue and remnants of cancer cells. A few normal acini are also present.

C: PET/CT of a mouse before and after treatment with a combination of Abraxane and Amy22 (representative pictures from treated cohort). The diminished uptake of 18F-FDG by remnants of PDA is evident (compare the size of dotted circles).

D: Histopathological features (H & E staining) of the treated tumor in (C). The analysis reveals the presence of scared fibrotic tissue, remnants of cancer cells and a larger area consisting of normal acini.

E: Gamma counting of the exact overall 18F-FDG uptake post-mortem reveals that the remaining tumor after treatment with Abraxane alone is 27% of that of untreated PDA tumors (not shown; see Stellas et al., 2014). The corresponding percentage after the combination treatment is 12.8%.

Conclusion: Amy22 enhances the efficacy of Abraxane that is currently the new gold standard of human PDA chemotherapy.

Figure 7:
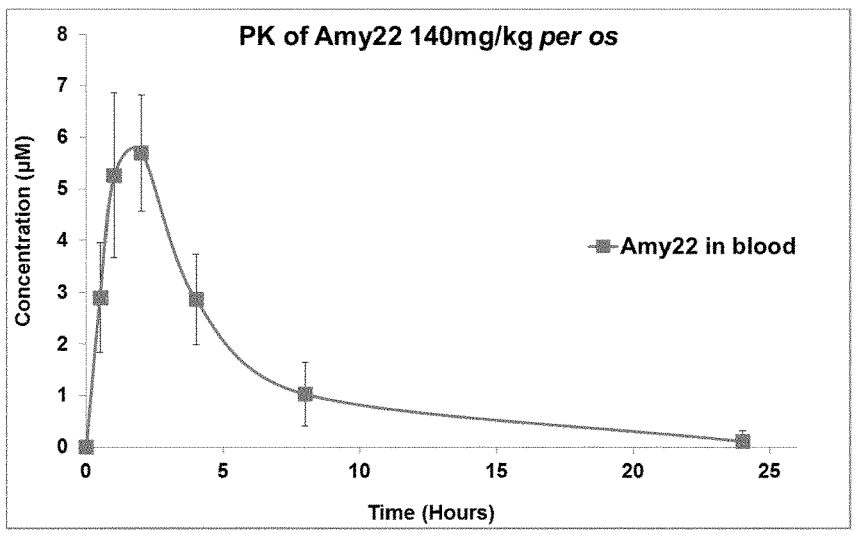

FIG. 7 Blood concentrations of the Amy22 compound following administration to mice by oral gavage (140 mg/kg in 0.5% CMC) and serial bleeding at the indicated times.

Figure 8:
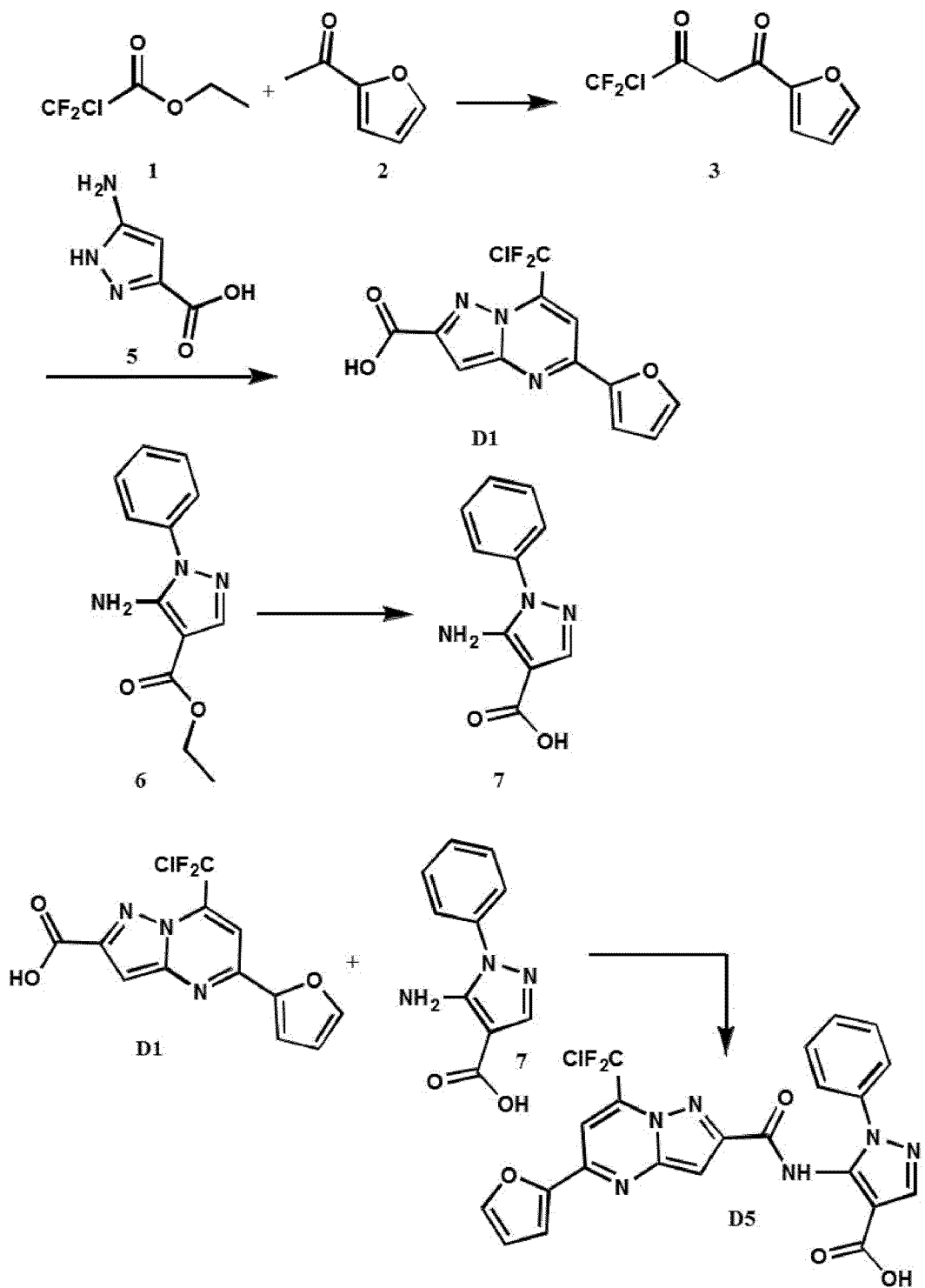

FIG. 8. Scheme for the synthesis of a compound according to the present invention (Amy22).

DETAILED DESCRIPTION OF THE INVENTION

Definitions

All terms used in the present application shall have the meaning usually employed by a relevant person skilled in the art, e.g. by a medicinal chemist, organic chemist, pharmacist, a molecular biologist, a physician, or a team thereof. By way of example, some definitions of specific terms are given below:

The articles "a" and "an" are used to refer to one or to more than one (i.e. to at least one) of the grammatical object of the article. For example, "a cell" means one cell or more than one cell.

"Alkyl" includes monovalent saturated aliphatic hydrocarbyl groups. The hydrocarbon chain may be either straight-chained or branched.

"Cancer" or "tumor" refers to the presence of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells may exist alone within an animal, or may be a non-tumorigenic cancer cell, such as a leukemia cell. As used herein, the term "cancer" includes premalignant as well as malignant cancers. "Cancerous diseases" or "cancers", which are used interchangeably herein, include, but are not limited to, acute monocytic leukemia, acute myelogenous leukemia, acute myelomonocytic leukemia, acute promyelocytic leukemia, adult T-cell leukemia, adult T-cell lymphoma, astrocytoma, atypical carcinoid lung cancer, basal cell carcinoma, B-acute lymphocytic leukemia, B-cell acute lymphoblastic leukemia/lymphoma, Bladder cancer, brain cancer, breast cancer, bronchial cancer, Burkitt's lymphoma, cancer of the bile duct, cancer of unknown primary origin, cervix cancer, chronic myeloproliferative disorder, colon cancer, diffuse large cell lymphoma, endometrial cancer, ependymoma, esophageal cancer, gastric cancer, glioma, glioblastoma, head and neck cancer, hemagiopericytoma, hepatocellular carcinoma, Hodgkin's lymphoma, Kaposi's sarcoma, kidney cancer, large cell neuroendocrine carcinoma, large granular lymphocytic leukemia, leukemia, liver cancer, lung cancer, lymphoma, medulloblastoma, melanoma, Multiple myeloma, myelodysplastic syndrome, nasopharygeal cancer, neuroblastoma, NK cell tumor, non-Hodgkin's lymphoma, oesophageal squamous cell carcinoma, osteosarcoma, ovarian cancer, pancreatic cancer, peripheral T-cell leukemia, primary plasma cell leukemia, prostate cancer, renal clear cell carcinoma, retinoblastoma, rhabdomyosarcoma, sarcoma, small cell lung carcinoma, T-cell acute lymphoblastic leukemia, T-cell acute lymphoblastic lymphoma, testicular cancer, thymoma, urachal cancer, uterine cancer, vaginal cancer, and the like.

An "agent inducing unscheduled DNA repair synthesis (UDS)" refers to any substance that leads to, preferably replication independent, unscheduled DNA repair synthesis (UDS) in the targeted region of an oncogene, such as Myc. One exemplary class of such agents are triple helix forming oligonucleotides (TFOs) which bind in the major groove of duplex DNA with high specificity and affinity, forming triple-helical DNA structures. They can be used to initiate site-specific DNA damage to stimulate UDS and allow for specific incorporation of nucleotides (or antimetabolites such as pyrimidine analogs, e.g. gemcitabine) into TFO-binding sites in target oncogenes. For example, Myc2T is a specific triplex-forming oligonucleotide (3'-TGGGTGGGTGGTTTGTTTTTGGG-5'), which binds the promoter 2 region of the human Myc gene (Boulware, S. B. et al., *Mol. Carcinogen*. published May 16, 2013, DOI: 10.1002/mc.22026).

"Cycloalkyl" refers to cyclic saturated aliphatic hydrocarbyl groups. The numbers of C-atoms referenced in connection with a given cycloalkyl group corresponds to the number of ring forming carbon atoms, e.g. "$C_6$ cycloalkyl" refers to a cyclohexyl. Preferably, cycloalkyls referenced herein are $C_6$-$C_{14}$ cycloalkyls.

"Cycloalkenyl" refers to cyclic unsaturated aliphatic hydrocarbyl groups. The numbers of C-atoms referenced in connection with a given cycloalkyl group correspond to the number of ring forming carbon atoms, e.g. "$C_6$ cycloalkyl" refers to a cyclohexenyl. In some embodiments, the cycloalkenyl comprises one double-bond. In some embodiments, the cyclohexenyl comprises more than one double bond, preferably two double bonds.

"Aryl" refers to any functional group or substituent derived from an aromatic ring, such as a phenyl, naphthyl, thienyl, or indolyl. In preferred embodiments, the aryl is a substituted or unsubstituted phenyl, pyridinyl, or pyrimidinyl, more preferably a phenyl or a pyridinyl, and even more preferably a phenyl. The substitution may be an atom or a molecule substituted in place of a hydrogen atom on the parent chain of a hydrocarbon. Suitable substituents are known to a skilled person in the field of chemistry, more specifically, medicinal or organic chemistry.

"Deregulation" refers to an alteration or modification of the expression of a gene that encodes an enzyme/protein in a biosynthetic pathway, such that the level or activity of said enzyme/protein is altered or modified, which is found in, but is not limited to, cancer cells.

"Furanyl" comprises a furan ring that can be bound by any C-atom.

"Halo" or "halogen" refers to fluoro, chloro, bromo and iodo. Preferred halo groups are either fluoro or chloro.

"Haloalkyl" includes an "alkyl" group as defined further above which is substituted with one or more halogens which may be the same or different.

"Hydrate" refers to a type of crystalline form which retains a certain number of water molecules as part of the solid crystalline structure.

"Metabolites" refer to the by-products of metabolism. The formation of metabolites critically depends on enzymes that act on a parent structure in vivo.

"Antimetabolites" refers to chemical that inhibits the use of a metabolite. Such substances are often similar in structure to the metabolite that they interfere with. The presence of antimetabolites can have toxic effects on cells, such as preventing or reducing cell growth and cell division. Therefore, such substances are used as chemotherapy for cancer.

"Neoplasm" refers to an abnormal mass of tissue as a result of abnormal growth or division of cells. It usually causes a lump or tumor. Neoplasms may be benign, pre-malignant (carcinoma in situ) or malignant (cancer).

"Overexpression" refers to an excessive expression of a gene, thereby producing an excess of its effect or product. Most cancers arise through the overexpression of key cellular regulatory genes.

"Prodrug" refers to a medication that is initially administered to the body in an inactive (or less than fully active) form, and then becomes converted to its active form through the normal metabolic processes of the body.

"Pyrazolyl" comprises a pyrazole ring that can be bound by any C-atom as well as by its nitrogen atom.

"Pyrrolyl" comprises a pyrrole ring that can be bound by any C-atom as well as by its nitrogen atom.

"Solvate" refers to a type of crystalline form which retains a certain number of solvent molecule other than water as part of the solid crystalline structure.

"Tautomers" refer to constitutional isomers of an organic compound that interconvert readily by a chemical reaction called tautomerization, which commonly results in the formal migration of a hydrogen atom or proton, accompanied by a switch of a single bond and adjacent double bond.

"Thiophenyl" comprises a thiophen ring that can be bound by any C-atom.

Any "alkyl", "cycloalkyl", "furanyl", "pyrrolyl", "thiophenyl", "aryl" or "phenyl" may be unsubstituted or substituted by one or more atoms or atom groups (molecules).

"Pharmaceutically acceptable" refers to being devoid of substantial toxic effects when used in doses usually employed in a medicinal dosage form, and thereby being approvable or preferably being approved by a regulatory agency of the Federal or a state government or being listed in the U. S. Pharmacopoeia or other generally recognized pharmacopoeia for use in animals, more preferably in humans.

"Pharmaceutically acceptable salt" refers to a salt of a compound of the invention that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2naphthalenesulfonic acid, 4-toluenesulfonic acid, camphorsulfonic acid, 4methylbicyclo [2.2.2]-oct-2-ene-I-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced, forming an ion pair with a positively-charged base moiety.

"Pharmaceutically acceptable carrier" refers to a diluent, adjuvant, excipient or carrier with which a compound of the invention is administered.

"Polymorphs" refer to different crystalline forms of the same compound. Polymorphism denotes the ability of a material to exist in more than one form or crystal structure.

"Preventing" or "prevention" refers to a reduction in risk of acquiring a disease or disorder (i. e., causing at least one of the clinical symptoms of the disease not to develop in a subject that may be exposed to or predisposed to the disease but does not yet experience or display symptoms of the disease).

"Therapeutically effective amount" refers to the amount of a compound that, when administered to a subject for treating a disease, is sufficient to effect such treatment for the disease. The "therapeutically effective amount" can vary depending on the compound, the disease and its severity, and the age, weight, etc., of the subject to be treated. Preferably, the compound according to the present invention may be used at a dose of from 0.1 to 200 mg/kg, more preferably at a dose of from 0.5 to 50.0 mg/kg. In any event, the suitable dose will be determined by those of skill in the art by appropriate routine dosing experiments carried out in the species intended to be treated.

"Treating" or "treatment" of any disease or disorder refers to, in one embodiment, to ameliorating the disease or disorder (i. e., arresting or reducing the development of the disease or at least one of the clinical symptoms thereof). In another embodiment, "treating" or "treatment" refers to ameliorating at least one physical parameter, which may not be discernible by the subject. In yet another embodiment, "treating" or "treatment" refers to modulating the disease or disorder, either physically, (e. g., stabilization of a discernible symptom), physiologically (e. g., stabilization of a physical parameter), or both. In yet another embodiment, "treating" or "treatment" refers to delaying the onset of the disease or disorder.

Compounds and Pharmaceutical Compositions

One aspect of the invention refers to a compound of formula (I)

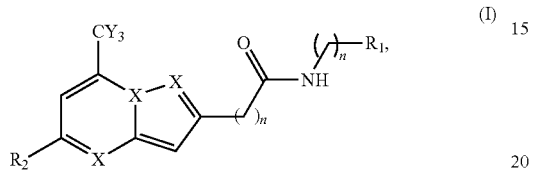

a tautomer, polymorph, hydrate, solvate, metabolite, prodrug, or a pharmaceutically acceptable salt thereof, wherein n is independently 0 or 1, preferably 1;
each X is independently C or N, preferably X is N;
Y is independently hydrogen, fluoro, chloro, or bromo; preferably fluoro or chloro;
$R_1$ and $R_2$, which may be the same or different, represent respectively

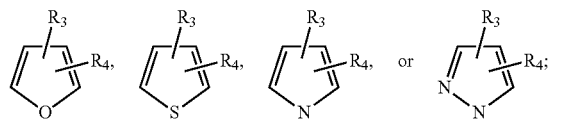

$R_3$ is a group —$R_5$—COOH (i.e. carboxyl) group or a pharmaceutically acceptable salt thereof; wherein $R_5$ is either a bond or a short ($C_1$, $C_2$, or $C_3$)-alkyl group; and $R_4$ is selected from any one of the following: substituted or unsubstituted ($C_5$-$C_{14}$) cycloalkyl or cycloalkenyl, preferably a cyclohexyl, heterocyclic alkyl or mono- or dialkenyl, or substituted or unsubstituted ($C_5$-$C_{14}$) aryl, preferably a phenyl, or substituted or unsubstituted ($C_5$-$C_{10}$) heteroaryl.

In some embodiments of this aspect of the invention, the compound of formula (I) is one wherein the residues are selected from the following:

n is 0;
X is, in each instance, N;
$CY_3$ is $CF_3$, $CF_2Cl$, or $CFCl_2$;
$R_1$ is

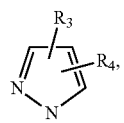

$R_2$ is 2-thiophenyl, 2-furanyl, 2-pyrrolyl or 5-pyrazolyl, preferably 2-thiophenyl or 2-furanyl;
$R_3$ is a group —$R_5$—COOH (i.e. carboxyl) group or a pharmaceutically acceptable salt thereof; wherein $R_5$ is a bond or a $C_1$ alkyl (i.e. —$CH_2$—) group;

$R_4$ is selected from any one of the following: substituted or unsubstituted cyclohexyl, substituted or unsubstituted tetrahydropyran, piperidine, thiacyclohexane, dioxane, piperazine, morpholine, pyran, oxazine, thiazine, substituted or unsubstituted phenyl, pyridine, or pyrimidine.

In some embodiments of this aspect, the compound of formula (I) is one wherein the residues are selected form the following:

n is 0;
X is, in each instance, N;
$CY_3$ is $CF_3$, $CF_2Cl$, or $CFCl_2$;
$R_1$ is

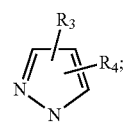

$R_2$ is 2-furanyl; and
$R_3$ is a carboxyl group directly attached to the pyrazole ring (i.e. wherein $R_5$ is a bond), or a pharmaceutically acceptable salt thereof; and
$R_4$ is a phenyl group.

In preferred embodiments, formula (I) refers to a compound having the following formula (II):

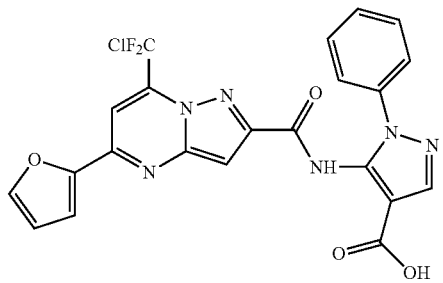

or a pharmaceutically acceptable salt thereof. This compound is also referred to herein as under its internal designation Amy22.

Due to the presence of the carboxyl group (or the corresponding carboxylate moiety when present in the form of a salt), the compounds of the invention can be formulated easily (also since the option to use various salt forms is available), thereby reducing intra/inter-subject variability when administered in oral dosage forms. Moreover, the compounds are, inter alia, characterized by excellent solubility and dissolution rates. These properties are expected to lead to high peak serum concentrations and excellent bioavailability, as has been demonstrated in vivo for, e.g., Amy22 (cf. FIG. 7).

Pharmaceutical Compositions

The invention further refers to pharmaceutical compositions comprising the compounds of formula (I) or, preferably, of formula (II) as depicted above. Optionally, they may further comprise one or more additional therapeutic (i.e. pharmaceutically active) agents.

In some embodiments, the one or more additional therapeutic agents of the pharmaceutical composition may be selected from the group (A) consisting of: 10-Hydroxycamptothecin, 17-Allylamino-geldanamycin, 2-Methoxyantimycin A3,3,4-Dichloroisocoumarin, 4-Hydroxyphenylretinamide, 9-cis Retinoic acid, Abiraterone, Ado-Trastuzumab Emtansine, Adriamycin, Afatinib, N-(3-chlorophenyl)-6,7-dimethoxyquinazolin-4-amine, 2-Amino-4-(1H-indol-5-yl)-1,1,3-tricyanobuta-1,3-diene, Aldesleukin, Alemtuzumab, Amifostine, Anastrozole, Anisomycin, Aphidicolin, Arsenic Trioxide, Asparaginase *Erwinia chrysanthemi*, Axitinib, N-[2(S)-(2(R)-2-Amino-3-mercaptopropylamino)-3-methylbutyl]-phenylalanyl-L-methionine trifluoroacetate salt, Bacillus Calmette-Guerin, bisphenol A diglycidyl ether, Bendamustine, Beta-lapachone, Betulinic acid, Bevacizumab, Bexarotene, Bicalutamide, BisBenzimide, Bleomycin, Bortezomib, Bosutinib, Buserelin, Busulfan, Cabazitaxel, Calpeptin, Camptothecin, Caffeic acid phenethyl ester, Capecitabine, Carboplatin, Carboplatin, Carfilzomib, Carmustine, Cetuximab, Chlorambucil, Ciglitazone, Cisplatin, Clodronate, Clofarabine, Crizotinib, Curcumin, Cyclo [Arg-Gly-Asp-D-Phe-Val], Cycloheximide, Cyclopamine, Cyclophosphamide, Cyclosporin A, Cyproterone, Cytarabine, D12-Prostaglandin J2, Dabrafenib, Dacarbazine, Dactinomycin, Dasatinib, Daunorubicin, Degarelix, Denosumab, Dexamethasone, Docetaxel, Doxorubicin, Ebselen, Ellipticine, Enzalutamide, Epirubicin, Erlotinib, Etoposide, Everolimus, Exemestane, Fludarabine, Fluorouracil, Flutamide, Folinic acid, Fulvestrant, Gefitinib, Geldanamycin, Gemcitabine, Genistein, Gingerol, Gliotoxin, Goserelin, 2-Chloro-5-nitrobenzanilide, 2-Amino-6-bromo-α-cyano-3-(ethoxycarbonyl)-4H-1-benzopyran-4-acetic acid ethyl ester, Hinokitiol, Sobuzoxane, Idarubicin, ifosfamide, Imatinib, Indomethacin, Ipilimumab, Irinotecan, Ixabepilone, Lanreotide, Lapatinib, Lenalidomide, Letrozole, Leucovorin, Leuprolide, Medroxyprogesterone, Megestrol, Melphalan, Mepesuccinate, Mercaptopurine, Mesna, Methotrexate, Methoxy verapamil, carbobenzoxy-L-leucyl-L-leucyl-L-leucinal, Mitomycin C, Mitoxantrone, N,N-Dimethylsphingosine, Nelarabine, Nilotinib, Octreotide, Ofatumumab, Oligomycin A, Omacetaxine, Oxaliplatin, Paclitaxel, Pamidronate, Panitumumab, Pazopanib, Pegaspargase, Pemetrexed, Pertuzumab, Pifithrin, plerixafor, Podophyllotoxin, Pomalidomide, Ponatinib, Prednisone, 2,2-Bis(hydroxymethyl)-1-azabicyclo[2.2.2]octan-3-one, Procarbazine, Radium 223 Dichloride, Raltitrexed, Rapamycin, Recombinant Human Papillomavirus (HPV) Bivalent Vaccine, Recombinant HPV Quadravalent Vaccine, Recombinant HPV Bivalent, Vaccine, Recombinant HPV Quadravalent Vaccine, Recombinant Interferon Alfa-2b, Regorafenib, Resveratrol, all trans Retinoic acid, Rheumatrex, Rituximab, Rolipram, Roscovitine, Rottlerin, Shikonin, Sipuleucel-T, Sirolimus, Sorafenib, Sphingosine, Splitomycin, Staurosporine, Stilboestrol, Streptozocin, 3-(4-Dimethylaminobenzylidenyl)-2-indolinone, 3-[[(4-Dimethylamino)phenyl]methylene]-1,3-dihydro-2H-indol-2-one, Sulindac sulphide, Sunitinib, Tamoxifen, Temozolomide, Temsirolimus, Thalidomide, Topotecan, Toremifene, Trametinib, Trastuzumab, Trichostatin-A, Trifluoperazine, 4-[(E)-2-(5,6,7,8-Tetrahydro-5,5,8,8-tetramethyl-2-naphthalenyl)-1-propenyl]benzoic acid, 3,4-Dihydroxy-α-cyanothiocinnam-amide, (3-Hydroxy-4-nitrobenzylidene) malononitrile, Valproic acid, Vemurafenib, Verapamil, Vinblastine, Vincristine, Vinorelbine, Wortmannin, 4-Chloro-6-(2,3-xylidino)-2-pyrimidinylthioacetic acid, Ziv-Aflibercept, Zoledronic Acid, salts thereof, and combinations thereof.

Preferably, the one or more therapeutic agents are selected from, but not restricted to, the group (A'), i.e. Abiraterone, Ado-Trastuzumab Emtansine, Afatinib, Anastrozole, Bevacizumab, Cabazitaxel, Capecitabine, Carboplatin, Cisplatin, Crizotinib, Cyclophosphamide, Degarelix, Denosumab, Docetaxel, Doxorubicin, Enzalutamide, Epirubicin, Erlotinib, Etoposide, Everolimus, Exemestane, Fluorouracil, Fulvestrant, Gefitinib, Gemcitabine, Ixabepilone, Lapatinib, Letrozole, Leuprolide, Megestrol, Methotrexate, Mitomycin C, Paclitaxel, Pamidronate, Pemetrexed, Pertuzumab, Prednisone, Radium 223 Dichloride, Sipuleucel-T, Sunitinib, Tamoxifen, Topotecan, Toremifene, Trastuzumab, salts thereof, and any combination thereof.

In some embodiments of this aspect of the present invention, the pharmaceutical compositions comprise, besides the compound of formula (I) or formula (II) described above, one or more additional therapeutic agent(s) selected from the group consisting of:

for Acute Lymphoblastic Leukemia (ALL):
Abitrexate (Methotrexate), Adriamycin PFS (Doxorubicin Hydrochloride), Adriamycin RDF (Doxorubicin Hydrochloride), Arranon (Nelarabine), Asparaginase *Erwinia chrysanthemi*, Cerubidine (Daunorubicin Hydrochloride), Clafen (Cyclophosphamide), Clofarabine, Clofarex (Clofarabine), Clolar (Clofarabine), Cyclophosphamide, Cytarabine, Cytosar-U (Cytarabine), Cytoxan (Cyclophosphamide), Dasatinib, Faunorubicin Hydrochloride, Doxorubicin Hydrochloride, Erwinaze (Asparaginase Erwinia hrysanthemi), Folex (Methotrexate), Folex PFS (Methotrexate), Gleevec (Imatinib Mesylate), Iclusig (Ponatinib Hydrochloride), Imatinib Mesylate, Marqibo (Vincristine Sulfate Liposome), Mercaptopurine, Methotrexate, Methotrexate LPF (Methorexate), Mexate (Methotrexate), Mexate-AQ (Methotrexate), Nelarabine, Neosar (Cyclophosphamide), Oncaspar (Pegaspargase), Pegaspargase, Purinethol (Mercaptopurine), Rubidomycin (Daunorubicin Hydrochloride), Sprycel (Dasatinib), Tarabine PFS (Cytarabine), Vincasar PFS (Vincristine Sulfate), Vincristine Sulfate, or Vincristine Sulfate Liposome;

for Acute Myeloid Leukemia (AML):
Adriamycin PFS (Doxorubicin Hydrochloride). Adriamycin RDF (Doxorubicin Hydrochloride), Arsenic Trioxide, Cerubidine (Daunorubicin Hydrochloride), Clafen (Cyclophosphamide), Cyclophosphamide, Cytarabine, Cytosar-U (Cytarabine), Cytoxan (Cyclophosphamide), Daunorubicin Hydrochloride, Doxorubicin Hydrochloride, Neosar (Cyclophosphamide), Rubidomycin (Daunorubicin Hydrochloride), Tarabine PFS (Cytarabine), Trisenox (Arsenic Trioxide), Vincasar PFS (Vincristine Sulfate), or Vincristine Sulfate;

for Chronic Lymphocytic Leukemia (CLL):
Alemtuzumab, Ambochlorin (Chlorambucil), Amboclorin (Chlorambucil), Arzerra (Ofatumumab), Bendamustine Hydrochloride, Campath (Alemtuzumab), Chlorambucil-Clafen (Cyclophosphamide), Cyclophosphamide, Cytoxan (Cyclophosphamide), Fludara (Fludarabine Phosphate), Fludarabine Phosphate, Leukeran (Chlorambucil), Linfolizin (Chlorambucil), Neosar (Cyclophosphamide), Ofatumumab, Treanda (Bendamustine Hydrochloride), Chlorambucil-Prednisone, or CVP (a combination of Cyclophosphamide, Vincristine and Prednisone);

for Chronic Myelogenous Leukemia (CML):
Bosulif (Bosutinib), Bosutinib, Clafen (Cyclophosphamide), Cyclophosphamide, Cytarabine, Cytosar-U (Cytarabine), Cytoxan (Cyclophosphamide), Dasatinib, Gleevec (Imatinib Mesylate), Iclusig (Ponatinib Hydrochloride), Imatinib Mesylate, Neosar (Cyclophosphamide), Nilotinib, Omacetaxine Mepesuccinate, Ponatinib Hydrochloride, Sprycel (Dasatinib), Synribo (Omacetaxine Mepesuccinate), Tarabine PFS (Cytarabine), or Tasigna (Nilotinib);

for Meningeal Leukemia:
Cytarabine, Cytosar-U (Cytarabine), or Tarabine PFS (Cytarabine);
for Burkitt's lymphoma:
Methotrexate (Anti-Rheumatic) oral, Rituxan iv, methotrexate sodium oral, dexamethasone oral, DexPak, rituximab iv, methotrexate sodium inj, Adriamycin iv, cyclophosphamide oral, Trexall oral, vincristine iv, cyclophosphamide iv, dexamethasone sodium phosphate inj, Dexamethasone Intensol oral, methotrexate sodium (PF) inj, Rheumatrex oral, cytarabine inj, doxorubicin iv, dexamethasone sodium phos (PF) inj, etoposide iv, ifosfamide iv, Ifex iv, cytarabine (PF) inj, Adriamycin PFS iv, DexPak 10 day oral, DexPak 6 Day oral, ifosfamide-mesna iv, Toposar iv, etoposide phosphate iv, Etopophos iv, Vincasar PFS iv, or Baycadron oral;
for diffuse large cell lymphoma:
prednisone oral, Rituxan iv, dexamethasone oral, DexPak 13 Day oral, rituximab iv, Adriamycin iv, cyclophosphamide oral, Prednisone Intensol oral, vincristine iv, cyclophosphamide iv, bleomycin inj, dexamethasone sodium phosphate inj, Dexamethasone Intensol oral, cytarabine inj, melphalan oral, doxorubicin iv, Alkeran oral, etoposide oral, dexamethasone sodium phos (PF) inj, melphalan iv, procarbazine oral, etoposide iv, cytarabine (PF) inj, Adriamycin PFS iv, DexPak 10 day oral, DexPak 6 Day oral, Rayos oral, Alkeran iv, Matulane oral, epirubicin iv, Toposar iv, etoposide phosphate iv, Etopophos iv, Ellence iv, Vincasar PFS iv, or Baycadron oral;
for Multiple Myeloma and Other Plasma Cell Neoplasms:
Aredia (Pamidronate Disodium), Bortezomib, Carfilzomib, Clafen (Cyclophosphamide), Cyclophosphamide, Cytoxan (Cyclophosphamide), Doxil (Doxorubicin Hydrochloride Liposome), Doxorubicin Hydrochloride Liposome, Dox-SL (Doxorubicin Hydrochloride Liposome), Evacet (Doxorubicin Hydrochloride Liposome), Kyprolis (Carfilzomib), Lenalidomide, LipoDox (Doxorubicin Hydrochloride Liposome), Mozobil (Plerixafor), Neosar (Cyclophosphamide), Pamidronate Disodium, Plerixafor, Pomalidomide (Pomalyst), Pomalyst, Revlimid (Lenalidomide), Synovir (Thalidomide), Thalidomide, Thalomid (Thalidomide), Velcade (Bortezomib), Zoledronic Acid, or Zometa (Zoledronic Acid);
for Non-Small Cell Lung Cancer:
Abitrexate (Methotrexate), Abraxane (Paclitaxel Albumin-stabilized Nanoparticle Formulation), Afatinib Dimaleate, Alimta (Pemetrexed Disodium), Avastin (Bevacizumab), Bevacizumab, Carboplatin, Cisplatin, Crizotinib, Erlotinib Hydrochloride, Folex (Methotrexate), Folex PFS (Methotrexate), Gefitinib, Gilotrif (Afatinib Dimaleate), Gemcitabine Hydrochloride, Gemzar (Gemcitabine Hydrochloride), Iressa (Gefitinib), Methotrexate, Methotrexate LPF (Methotrexate), Mexate (Methotrexate), Mexate-AQ (Methotrexate), Paclitaxel, Paclitaxel Albumin-stabilized Nanoparticle Formulation, Paraplat (Carboplatin), Paraplatin (Carboplatin), Pemetrexed Disodium, Platinol (Cisplatin), Platinol-AQ (Cisplatin), Tarceva (Erlotinib Hydrochloride), Taxol (Paclitaxel), Xalkori (Crizotinib), a combination of Carboplatin-Taxol, or a combination of Gemcitabine-Cisplatin;
for Small Cell Lung Cancer:
Abitrexate (Methotrexate), Etopophos (Etoposide Phosphate), Etoposide, Etoposide Phosphate, Folex (Methotrexate), Folex PFS (Methotrexate), Hycamtin (Topotecan Hydrochloride), Methotrexate, Methotrexate LPF (Methotrexate), Mexate (Methotrexate), Mexate-AQ (Methotrexate), Toposar (Etoposide), Topotecan Hydrochloride, or VePesid (Etoposide);
for bladder cancer:
Adriamycin PFS (Doxorubicin Hydrochloride), Adriamycin RDF (Doxorubicin Hydrochloride), Cisplatin, Doxorubicin Hydrochloride, Platinol (Cisplatin), or Platinol-AQ (Cisplatin);
for breast cancer:
Perjeta (pertuzumab), Abitrexate (Methotrexate), Abraxane (Paclitaxel Albumin-stabilized Nanoparticle Formulation), Ado-Trastuzumab Emtansine, Adriamycin PFS (Doxorubicin Hydrochloride), Adriamycin RDF (Doxorubicin Hydrochloride), Adrucil (Fluorouracil), Afinitor (Everolimus), Anastrozole, Aredia (Pamidronate Disodium), Arimidex (Anastrozole), Aromasin (Exemestane), Capecitabine, Clafen (Cyclophosphamide), Cyclophosphamide, Cytoxan (Cyclophosphamide), Docetaxel, Doxorubicin Hydrochloride, Efudex (Fluorouracil), Ellence (Epirubicin Hydrochloride), Epirubicin Hydrochloride, Everolimus, Exemestane, Fareston (Toremifene), Faslodex (Fulvestrant), Femara (Letrozole), Fluoroplex (Fluorouracil), Fluorouracil, Folex (Methotrexate), Folex PFS (Methotrexate), Fulvestrant, Gemcitabine Hydrochloride, Gemzar (Gemcitabine Hydrochloride), Herceptin (Trastuzumab), Ixabepilone, Ixempra (Ixabepilone), Kadcyla (Ado-Trastuzumab Emtansine), Lapatinib Ditosylate, Letrozole, Megace (Megestrol Acetate), Megestrol Acetate, Methotrexate, Methotrexate LPF (Methotrexate), Mexate (Methotrexate), Mexate-AQ (Methotrexate), Neosar (Cyclophosphamide), Nolvadex (Tamoxifen Citrate), Novaldex (Tamoxifen Citrate), Paclitaxel, Paclitaxel Albumin-stabilized Nanoparticle Formulation, Pamidronate Disodium, Perjeta (Pertuzumab), Pertuzumab, Tamoxifen Citrate, Taxol (Paclitaxel), Taxotere (Docetaxel), Trastuzumab, Toremifene, Tykerb (Lapatinib Ditosylate), or Xeloda (Capecitabine);
for cervical cancer:
Blenoxane (Bleomycin), Bleomycin, Cisplatin, Hycamtin (Topotecan Hydrochloride), Platinol (Cisplatin), Platinol-AQ (Cisplatin), Topotecan Hydrochloride, or a combination of Gemcitabine-Cisplatin;
for colon cancer:
Adrucil (Fluorouracil), Avastin (Bevacizumab), Bevacizumab, Camptosar (Irinotecan Hydrochloride), Capecitabine, Cetuximab, Efudex (Fluorouracil), Eloxatin (Oxaliplatin), Erbitux (Cetuximab), Fluoroplex (Fluorouracil), Fluorouracil, Irinotecan Hydrochloride, Leucovorin Calcium, Oxaliplatin, Panitumumab, Regorafenib, Stivarga (Regorafenib), Vectibix (Panitumumab), Wellcovorin (Leucovorin Calcium), Xeloda (Capecitabine), Zaltrap (Ziv-Aflibercept), Ziv-Aflibercept, CAPDX (a combination of capecitabine and oxaliplatin.), FOLFIRI (a combination of Folinic acid, Fluorouracil, and Irinotecan), FOLFIRI-Bevacizumab (a combination of Folinic acid, Fluorouracil, Irinotecan, and Bevacizumab), FOLFIRI-Cetuximab (a combination of Folinic acid, Fluorouracil, Irinotecan, and Cetuximab), FOLFOX (a combination of Folinic acid, Fluorouracil, and Oxaliplatin), or XELOX (a combination of Capecitabine and Oxaliplatin);
for rectal cancer:
Adrucil (Fluorouracil), Avastin (Bevacizumab), Bevacizumab, Camptosar (Irinotecan Hydrochloride), Cetuximab, Efudex (Fluorouracil), Erbitux (Cetuximab), Fluoroplex (Fluorouracil), Fluorouracil, Irinotecan Hydrochloride, Panitumumab, Regorafenib, Stivarga (Regorafenib), Vectibix (Panitumumab), Zaltrap (Ziv-Aflibercept), Ziv-Aflibercept, CAPDX, FOLFIRI, FOLFIRI-Bevacizumab, FOLFIRI-Cetuximab, FOLFOX, or XELOX;

for gastric cancer:
Adriamycin PFS (Doxorubicin Hydrochloride), Adriamycin RDF (Doxorubicin Hydrochloride), Adrucil (Fluorouracil), Docetaxel, Doxorubicin Hydrochloride, Efudex (Fluorouracil), Fluoroplex (Fluorouracil), Fluorouracil, Herceptin (Trastuzumab), Mitomycin C, Mitozytrex (Mitomycin C), Mutamycin (Mitomycin C), Taxotere (Docetaxel), or Trastuzumab;
for glioblastoma:
Avastin (Bevacizumab), Temodar oral, vincristine iv, Camptosar iv, irinotecan iv, bevacizumab iv, temozolomide oral, Gliadel Wafer impl, procarbazine oral, BiCNU iv, Temodar iv, Matulane oral, Vincasar PFS iv, carmustine iv, carmustine in polifeprosan impl, or temozolomide iv;
for hepatocellular carcinoma:
Sorafenib, Sunitinib, Erlotinib, Bevacizumab, or Sirolimus;
for large cell neuroendocrine carcinoma:
sunitinib (Sutent), everolimus (Afinitor), or the combination of fluorouracil (Adrucil, 5-FU), doxorubicin (Adriamycin), and streptozocin (Zanosar);
for melanoma:
Aldesleukin, Dabrafenib, Dacarbazine, DTIC-Dome (Dacarbazine), Intron A (Recombinant Interferon Alfa-2b), Ipilimumab, Mekinist (Trametinib), Peginterferon Alfa-2b, PEG-Intron (Peginterferon Alfa-2b), Proleukin (Aldesleukin), Recombinant Interferon Alfa-2b, Sylatron (Peginterferon Alfa-2b), Tafinlar (Dabrafenib), Trametinib, Vemurafenib, Yervoy (Ipilimumab), or Zelboraf (Vemurafenib);
for neuroblastoma:
Adriamycin PFS (Doxorubicin Hydrochloride), Adriamycin RDF (Doxorubicin Hydrochloride), Clafen (Cyclophosphamide), Cyclophosphamide, Cytoxan (Cyclophosphamide), Doxorubicin Hydrochloride, Neosar (Cyclophosphamide), Vincasar PFS (Vincristine Sulfate), or Vincristine Sulfate;
for ovarian cancer:
Adriamycin PFS (Doxorubicin Hydrochloride), Adriamycin RDF (Doxorubicin Hydrochloride), Carboplatin, Clafen (Cyclophosphamide), Cisplatin, Cyclophosphamide, Cytoxan (Cyclophosphamide), Doxorubicin Hydrochloride, Dox-SL (Doxorubicin Hydrochloride Liposome), DOXIL (Doxorubicin Hydrochloride Liposome), Doxorubicin Hydrochloride Liposome, Evacet (Doxorubicin Hydrochloride Liposome), Gemcitabine Hydrochloride, Gemzar (Gemcitabine Hydrochloride), Hycamtin (Topotecan Hydrochloride), LipoDox (Doxorubicin Hydrochloride Liposome), Neosar (Cyclophosphamide), Paclitaxel, Paraplat (Carboplatin), Paraplatin (Carboplatin), Platinol (Cisplatin), Platinol-AQ (Cisplatin), Taxol (Paclitaxel), Topotecan Hydrochloride, BEP (a combination of Bleomycin, Etoposide, and Cisplatin), or a combination of Carboplatin-Taxol, or a combination of Gemcitabine-Cisplatin;
for pancreatic cancer:
Abraxane, Nab-Paclitaxel, Sunitinib, Everolimus, Adrucil (Fluorouracil), Efudex (Fluorouracil), Erlotinib Hydrochloride, Fluoroplex (Fluorouracil), Fluorouracil, Gemcitabine Hydrochloride, Gemzar (Gemcitabine Hydrochloride), Mitomycin C, Mitozytrex (Mitomycin C), Mutamycin (Mitomycin C), or Tarceva (Erlotinib Hydrochloride);
for penile cancer:
Blenoxane (Bleomycin), or Bleomycin;
for prostate cancer:
Abiraterone Acetate, Cabazitaxel, Degarelix, Denosumab, Docetaxel, Enzalutamide, Jevtana (Cabazitaxel), Leuprolide Acetate, Lupron (Leuprolide Acetate), Lupron Depot (Leuprolide Acetate), Lupron Depot-3 Month (Leuprolide Acetate), Lupron Depot-4 Month (Leuprolide Acetate), Lupron Depot-Ped (Leuprolide Acetate), Prednisone, Prolia (Denosumab), Provenge (Sipuleucel-T), Radium 223 Dichloride, Sipuleucel-T, Taxotere (Docetaxel), Viadur (Leuprolide Acetate), Xgeva (Denosumab), Xofigo (Radium 223 Dichloride), Xtandi (Enzalutamide), or Zytiga (Abiraterone Acetate);
for renal clear cell carcinoma:
Afinitor (Everolimus), Aldesleukin, Avastin (Bevacizumab), Axitinib, Bevacizumab, Everolimus, Inlyta (Axitinib), Nexavar (Sorafenib Tosylate), Pazopanib Hydrochloride, Proleukin (Aldesleukin), Sorafenib Tosylate, Sunitinib Malate, Sutent (Sunitinib Malate), Temsirolimus, Torisel (Temsirolimus), or Votrient (Pazopanib Hydrochloride);
for retinoblastoma:
Clafen (Cyclophosphamide), Cyclophosphamide, Cytoxan (Cyclophosphamide), or Neosar (Cyclophosphamide);
for rhabdomyosarcoma:
Cosmegen (Dactinomycin), Dactinomycin, Vincasar PFS (Vincristine Sulfate), or Vincristine Sulfate, and
for the prevention of Cervical Cancer:
Cervarix (Recombinant Human Papillomavirus (HPV) Bivalent Vaccine), Gardasil (Recombinant HPV Quadrivalent Vaccine), Recombinant HPV Bivalent Vaccine, Recombinant HPV Quadrivalent Vaccine.

In some embodiments of this aspect of the present invention, the pharmaceutical composition comprises a compound of formula (I), or preferably the compound having the formula (II), and, alternatively or in addition to the additional therapeutic agents of groups (A) or (A') as set out above, one or more additional therapeutic agent(s) selected from the group (B) consisting of:
Acetylsalicylic acid, Diflunisal, Salsalate, Ibuprofen, Dexibuprofen, Naproxen, Fenoprofen, Ketoprofen, Dexketoprofen, Flurbiprofen, Oxaprozin, Loxoprofen, Indomethacin, Tolmetin, Sulindac, Etodolac, Ketorolac, Diclofenac, Nabumetone, Piroxicam, Meloxicam, Tenoxicam, Droxicam, Lornoxicam, Isoxicam, Mefenamic acid, Meclofenamic acid, Flufenamic acid, Tolfenamic acid, Celecoxib, Rofecoxib, Valdecosib, Parecoxib, Lumiracoxib, Etoricoxib, Firocoxib, Nimesulide, Licofelone, H-harpagide, Lysine clonixinate, salts thereof, and combinations thereof. Preferably, the one or more additional therapeutic agent(s) in this aspect is a selective cyclooxygenase-2 (COX-2) inhibitor. Accordingly, in some preferred embodiments, the additional therapeutic agent is selected from the group (B') consisting of Celecoxib, Rofecoxib, Valdecosib, Parecoxib, Lumiracoxib, Etoricoxib, Firocoxib, pharmaceutically acceptable salts thereof, and combinations thereof.

In some embodiments of this aspect of the present invention, the pharmaceutical composition comprises a compound of formula (I) or formula (II) as described above and, alternatively or in addition to the additional therapeutic agents of groups (A), (A'), (B) or (B') as set out above, also one or more agents inducing unscheduled DNA repair synthesis (UDS) at a target oncogene. A target oncogene is typically one that is involved in the inducement or progression of cancer, such as Myc.

One example of UDS inducing agents are triple helix forming oligonucleotides (TFOs) which induce site-specific DNA damage at the target site of the selected oncogene. One exemplary TFO targeting Myc is a nucleotide having the sequence (3'-TGGGTGGGTGGTTTGTTTTTGGG-5') referred to herein as Myc2T, although it is readily apparent that other TFOs specifically binding to the targeting oncogene can be constructed with the knowledge of the nucleotide sequence of the oncogene in question.

In some embodiments, the TFOs may be administered separately. In other embodiments, the TFOs may be added to any of the above discussed compounds or pharmaceutical compositions, which may additionally include the above discussed additional therapeutic agents selected from the above-defined groups A, A', B and/or B'. The TFOs are particularly effective in combination with antimetabolite therapy (e.g. purine or pyrimidine analogs such as gemcitabine) and hence preferably administered in combination with such antimetabolite therapeutics.

Thus, the antimetabolite in the pharmaceutical compositions is in some embodiments preferably selected from purine or pyrimidine analogs, more preferably wherein the antimetabolite is selected from 5-fluorouracil, floxuridine, gemcitabine, cytarabine, or 6-azauracil.

In certain preferred embodiments of this aspect of the invention, the additional therapeutic agent in the pharmaceutical composition is selected from 5-fluorouracil, floxuridine, gemcitabine, cytarabine, 6-azauracil, and the triple helix forming oligonucleotide is Myc2T (SEQ ID NO: 1).

Pharmaceutical Formulations

Another aspect of the present invention relates to a pharmaceutical formulation comprising a compound of formula (I) or, preferably, formula (II), or a pharmaceutical composition as described above (which may additionally comprise the above-referenced additional therapeutic agents, TFOs and/or antimetabolites), and at least one pharmaceutically acceptable carrier.

The at least one pharmaceutically acceptable carrier is selected from the group consisting of peanut oil, sesame oil, cottonseed oil, corn oil, olive oil and mixtures of oils; ethyl oleate, isopropyl myristate, fatty acid glycerides, acetylated fatty acid glycerides; ethanol, isopropyl alcohol, hexadecyl alcohol, glycerol and propylene glycol, polyethyleneglycol, mineral oil, petrolatum; water, sterilized water, Ringer's solution, an isotonic aqueous saline solution, a dextrose solution, a glucose solution; β-cyclodextrin, hydroxypropyl-β-cyclodextrin; microcrystalline cellulose, crystalline cellulose, hydroxypropyl cellulose, hydroxypropyl methyl cellulose, methyl cellulose, carboxymethyl cellulose, sodium carboxymethyl cellulose, calcium carboxymethyl cellulose, cellulose acetate phthalate, cellulose acetate butyrate, hydroxyethyl cellulose, ethyl cellulose; and combinations thereof.

In preferred embodiments, the pharmaceutically acceptable carrier is selected from the group consisting of β-cyclodextrin, hydroxypropyl-β-cyclodextrin, hydroxypropyl cellulose, hydroxypropyl methyl cellulose, methyl cellulose, carboxymethyl cellulose, hydroxyethyl cellulose, ethyl cellulose, and combinations thereof. In certain preferred embodiments, the pharmaceutically acceptable carrier is selected from the group consisting of hydroxypropyl-β-cyclodextrin, carboxymethyl cellulose. and combinations thereof.

The above referenced compounds, preferably the compound having the formula (II), or pharmaceutical formulations comprising a compound of any compound referred to above, preferably compound having the formula (II), comprise at least one pharmaceutically acceptable carrier as described above, whereby the said formulations are typically in the form of a capsule, cachet, tablet, lozenge, powder, granule, oral suspension or solution.

Methods of Treatment Involving the Compounds of Formula (I)

A further aspect of the present invention relates to a method of treating or preventing a cancerous disease in a mammal, comprising the administration of a therapeutically effective amount of the compound of the present invention, of the pharmaceutical composition of the present invention, or of the pharmaceutical formulation of the present invention to the mammal in need of such treatment.

The compound of formula (I), the pharmaceutical composition, or the pharmaceutical formulation of the present invention is preferably administered by a route selected from the group consisting of oral, buccal, sublingual, transdermal, transmucosal, intranasal, intravenous, intraperitoneal, intramuscular, subcutaneous and intrathecal administration, preferably by a route of oral, buccal, or sublingual administration.

In some embodiments of this aspect, the method further comprises the separate (including partially overlapping in time, and sequentially) or concomitant administration of one or more additional therapeutic agent(s) as described above, and optionally further comprises the separate or concomitant administration of one or more agents inducing unscheduled DNA repair synthesis (UDS) in a target oncogene, such as Myc2T. The latter UDS-inducing agents are particularly preferred in combination with antimetabolites as the additional therapeutic agent (.e.g. gemcitabine), as described above.

Preferably, the additional therapeutic agent(s) is/are selected from a group (A) as described above, and optionally includes said one or more agents inducing unscheduled DNA repair synthesis (UDS), such as the triplet forming oligonucleotide Myc2T. In particularly preferred embodiments, the additional therapeutic agent(s) is/are selected from the group (A') described above.

In other embodiments of this aspect of the present invention, the additional therapeutic agent(s) is/are selected from the group (B) as described above. Preferably the additional therapeutic agent is one of the selective COX-2 inhibitors or selected from the group (B') as described above.

The method of treatment as described hereinabove may also comprise a further treatment selected from radiation therapy, surgery, or combinations thereof. Said further treatment may occur before or after the administration of the compound of formula (I), the pharmaceutical composition, or the pharmaceutical formulation as described herein.

The cancerous disease to be treated or prevented in the above aspects of the present invention is preferably susceptible to Myc overexpression and/or deregulation.

Preferably, the cancerous disease to be treated or prevented in the above aspects of the present invention is selected from the group (C) consisting of:
acute monocytic leukemia, acute myelogenous leukemia, acute myelomonocytic leukemia, acute promyelocytic leukemia, adult T-cell leukemia, adult T-cell lymphoma, astrocytoma, atypical carcinoid lung cancer, basal cell carcinoma, B-acute lymphocytic leukemia, B-cell acute lymphoblastic leukemia/lymphoma, Bladder cancer, brain cancer, breast cancer, bronchial cancer, Burkitt's lymphoma, cancer of the bile duct, cancer of unknown primary origin, cervix cancer, chronic myeloproliferative disorder, colon cancer, diffuse large cell lymphoma, endometrial cancer, ependymoma, esophageal cancer, gastric cancer, glioma, glioblastoma, head and neck cancer, hemagiopericytoma, hepatocellular carcinoma, Hodgkin's lymphoma, Kaposi's sarcoma, kidney cancer, large cell neuroendocrine carcinoma, large granular lymphocytic leukemia, leukemia, liver cancer, lung cancer, lymphoma, medulloblastoma, melanoma, Multiple myeloma, myelodysplastic syndrome, nasopharygeal cancer, neuroblastoma, NK cell tumor, non-Hodgkin's lymphoma, oesophageal squamous cell carcinoma, osteosarcoma, ovarian cancer, pancreatic cancer, peripheral T-cell leukemia, primary plasma cell leukemia, prostate cancer, renal clear cell carcinoma, retinoblastoma, rhabdomyosarcoma, sarcoma, small cell lung carcinoma, T-cell acute lymphoblastic leukemia, T-cell acute lymphoblastic lymphoma, testicular cancer, thymoma, urachal cancer, uterine cancer, vaginal cancer, and combinations thereof.

More preferably, the cancerous disease is selected from the group (C') consisting of B-acute lymphocytic leukemia, Burkitt's lymphoma, diffuse large cell lymphoma, multiple myeloma, primary plasma cell leukemia, atypical carcinoid lung cancer, bladder cancer, breast cancer, cervix cancer, colon cancer, gastric cancer, glioblastoma, hepatocellular carcinoma, large cell neuroendocrine carcinoma, medulloblastoma, melanoma, neuroblastoma, oesophageal squamous cell carcinoma, osteosarcoma, ovarian cancer, prostate cancer, renal clear cell carcinoma, retinoblastoma, rhabdomyosarcoma, small cell lung carcinoma, and combinations thereof.

The compound of formula (I), the pharmaceutical compositions or the pharmaceutical formulations as described herein above have been found to be particularly suitable for treating or preventing a cancerous disease selected from the group consisting of pancreatic cancer, breast cancer, prostate cancer, and lung cancer, preferably particularly pancreatic cancer or breast cancer.

In certain embodiments of the above aspects of the present invention, the cancerous disease is an adenocarcinoma. Preferably, the cancerous disease is in these embodiments selected from the group consisting of:
colon adenocarcinoma, lung adenocarcinoma, prostatic adenocarcinoma, urachal adenocarcinoma, vaginal adenocarcinoma, mammary adenocarcinoma, esophageal adenocarcinoma, bronchial adenocarcinoma, pancreatic adenocarcinoma, and gastrointestinal adenocarcinoma.

More preferably, the cancerous disease to be treated or prevented is a pancreatic ductal adenocarcinoma, mammary adenocarcinoma, prostatic adenocarcinoma, or lung adenocarcinoma and most preferably selected from pancreatic ductal adenocarcinoma, mammary adenocarcinoma, and lung adenocarcinoma.

Compounds and Pharmaceutical Compositions for Use in Medicine

Another aspect of the invention relates to the compounds of formula (I) or, preferably of formula (II), the pharmaceutical compositions (optionally comprising one or more additional therapeutic agent(s), TFOs, and/or antimetabolites), or the pharmaceutical formulations comprising the compounds or pharmaceutical compositions referred to above for use in medicine.

In some embodiments, said compounds, compositions and formulations are preferably used for treating or preventing a cancerous disease in a mammal. The mammal is preferably human.

In preferred embodiments, said compounds, compositions and formulations for the above-referenced medical use comprise a therapeutically effective amount of the above referenced compounds of formula (I) for administration to a subject in need thereof.

Any of the compounds of formula (I) described herein, preferably the compound of formula (II), the pharmaceutical composition, or the pharmaceutical formulation of the present invention, both preferably comprising the compound having the formula (II), is preferably administered by a route selected from the group consisting of oral, buccal, sublingual, transdermal, transmucosal, intranasal, intravenous, intraperitoneal, intramuscular, subcutaneous and intrathecal administration, preferably by a route of oral, buccal, or sublingual administration.

In some embodiments of said aspect of the invention, the compounds, pharmaceutical compositions, or pharmaceutical formulations comprising such compounds or pharmaceutical compositions, may be administered separately or concomitantly. In preferred embodiments, the TFO targets Myc and has the sequence (3'-TGGGTGGGTGGTTT-GTTTTTGGG-5', SEQ ID NO:1) referred to herein as Myc2T.

The above UDS-inducing agents are preferably used in combination with antimetabolites as an additional therapeutic agent (e.g. gemcitabine), as described above in the section relating to the compounds and the pharmaceutical compositions. Preferably, the additional therapeutic agent(s) is/are selected from a group (A) as described above in the compounds and pharmaceutical compositions section, and optionally include(s) said one or more agents inducing unscheduled DNA repair synthesis (UDS), such as the triplet forming oligonucleotide Myc2T. In particularly preferred embodiments, the additional therapeutic agent(s) is/are selected from the group (A') as described above in the compounds and pharmaceutical compositions section.

In other embodiments of this aspect of the present invention, the additional therapeutic agent(s) is/are additionally or alternatively selected from the group (B) as described above in the compounds and pharmaceutical compositions section. Preferably, the additional therapeutic agent is one of the selective COX-2 inhibitors selected from the group (B') as described.

With regard to the compounds, pharmaceutical compositions, or the pharmaceutical formulations for the uses described herein, the one or more additional therapeutic agent(s) or one or more agents inducing unscheduled DNA repair synthesis (UDS) is/are generally administered at the same time, i.e. concomitantly. Alternatively, they may be administered separately (including partially overlapping in time, and sequentially).

In some embodiments, the compounds, pharmaceutical compositions, or the formulations comprising the compounds or pharmaceutical compositions referred to above are used in treating of a cancerous disease which is susceptible to Myc overexpression and/or deregulation.

Preferably, the cancerous disease to be treated or prevented in the above embodiments of the present invention is selected from the group (C) consisting of: acute monocytic leukemia, acute myelogenous leukemia, acute myelomonocytic leukemia, acute promyelocytic leukemia, adult T-cell leukemia, adult T-cell lymphoma, astrocytoma, atypical carcinoid lung cancer, basal cell carcinoma, B-acute lymphocytic leukemia, B-cell acute lymphoblastic leukemia/lymphoma, Bladder cancer, brain cancer, breast cancer, bronchial cancer, Burkitt's lymphoma, cancer of the bile duct, cancer of unknown primary origin, cervix cancer, chronic myeloproliferative disorder, colon cancer, diffuse large cell lymphoma, endometrial cancer, ependymoma, esophageal cancer, gastric cancer, glioma, glioblastoma, head and neck cancer, hemagiopericytoma, hepatocellular carcinoma, Hodgkin's lymphoma, Kaposi's sarcoma, kidney cancer, large cell neuroendocrine carcinoma, large granular lymphocytic leukemia, leukemia, liver cancer, lung cancer, lymphoma, medulloblastoma, melanoma, Multiple myeloma, myelodysplastic syndrome, nasopharygeal cancer, neuroblastoma, NK cell tumor, non-Hodgkin's lymphoma, oesophageal squamous cell carcinoma, osteosarcoma, ovarian cancer, pancreatic cancer, peripheral T-cell leukemia, primary plasma cell leukemia, prostate cancer, renal clear cell carcinoma, retinoblastoma, rhabdomyosarcoma, sarcoma, small cell lung carcinoma, T-cell acute lymphoblastic leukemia, T-cell acute lymphoblastic lymphoma, testicular cancer, thymoma, urachal cancer, uterine cancer, vaginal cancer, and combinations thereof.

More preferably, the cancerous disease is selected from the group (C') consisting of B-acute lymphocytic leukemia, Burkitt's lymphoma, diffuse large cell lymphoma, multiple myeloma, primary plasma cell leukemia, atypical carcinoid lung cancer, bladder cancer, breast cancer, cervix cancer, colon cancer, gastric cancer, glioblastoma, hepatocellular carcinoma, large cell neuroendocrine carcinoma, medulloblastoma, melanoma, neuroblastoma, oesophageal squamous cell carcinoma, osteosarcoma, ovarian cancer, prostate cancer, renal clear cell carcinoma, retinoblastoma, rhabdomyosarcoma, small cell lung carcinoma, and combinations thereof.

The compounds, preferably the compound of formula (II), the pharmaceutical compositions or the pharmaceutical formulations comprising the compounds or the pharmaceutical compositions as described herein above have been found to be particularly suitable for use in treating a cancerous disease selected from the group consisting of pancreatic cancer, breast cancer, prostate cancer, and lung cancer, preferably particularly pancreatic cancer, or breast cancer.

In some embodiments of the above aspects of the present invention, the cancerous disease is an adenocarcinoma. Preferably, the cancerous disease is in these embodiments selected from the group consisting of: colon adenocarcinoma, lung adenocarcinoma, prostatic adenocarcinoma, urachal adenocarcinoma, vaginal adenocarcinoma, mammary adenocarcinoma, esophageal adenocarcinoma, bronchial adenocarcinoma, pancreatic adenocarcinoma, and gastrointestinal adenocarcinoma.

More preferably, the cancerous disease to be treated or prevented is a pancreatic ductal adenocarcinoma, mammary adenocarcinoma, prostatic adenocarcinoma, or lung adenocarcinoma, and most preferably selected from pancreatic ductal adenocarcinoma, mammary adenocarcinoma, and lung adenocarcinoma.

Method for the Manufacture of Compounds of Formula (I)

Another aspect of the invention refers to a method for the manufacture of any compound of formula (I) described herein. In general, the compounds of formula (I) are prepared by forming an amide between a 2-carboxyl-substituted bicyclic moiety of formula (III):

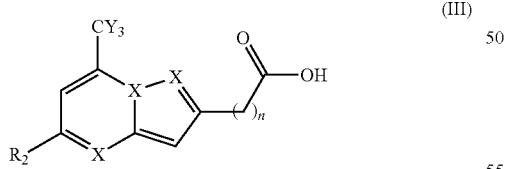

(III)

wherein X, $R_2$, and $Y_3$ and n are as defined above in formula (I) (e.g. compound D1 in FIG. 8/Example 8), and a moiety $R_1$ as defined in formula (I) above but carrying an extra amino group (e.g. compound (7) in FIG. 8/Example 8) to give the corresponding amide of formula (I). Optionally, the compound of formula (I) is subsequently converted to the corresponding, pharmaceutically acceptable salt form.

In a preferred embodiment, the method relates to the preparation of the compound of formula (II), or its pharmaceutically acceptable salt, by reacting a compound of formula (D1)

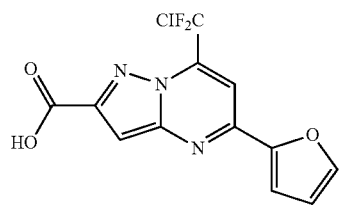

D1 with a compound of formula (7)

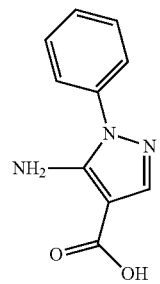

7 to yield the compound of formula (II), and, optionally, converting it to its corresponding salt form.

Preferably, the compounds of formula (I), and in particular of formula (II), may be synthesized according to the route depicted in FIG. 8 (cf. Example 8 for details on the reaction conditions, solvents etc.). In this regard, it will be readily apparent to the person of skill in the art how to synthesize compounds of formula (I) other than the compound of formula (II) by carrying out similar reaction steps with the respective intermediates, analogously to the reaction scheme shown in FIG. 8.

Having described the various aspects of the present invention in general terms, it will be apparent to those of skill in the art that many modifications and slight variations are possible without departing from the spirit and scope of the present invention. The present invention is now further described by reference to the following, non-limiting numbered embodiments.

EXAMPLES

Example 1: Cell Viability Data of TGR-1 and H015.19 Cells, Depending on Amy22 Conc To evaluate the in vitro activity of the compound having the formula (II) (Amy22), the sibling cell lines TGR-1 and H015.19 were used. The TGR-1 cells are a subclone of the Rat-1 fibroblastic cell line with intact Myc ($Myc^{+/+}$), whereas the H015.19 cells are $Myc^{-/-}$ derivatives of the TGR-1 cells (Mateyak et al., 1997). The two sibling cell lines thus differ only in the presence or absence of Myc, thereby allowing to determine not only the activity of the tested compound in Myc-positive cancer cells, but also in cells not expressing Myc offering an indication of the specificity of the tested compound.

Figure 1:
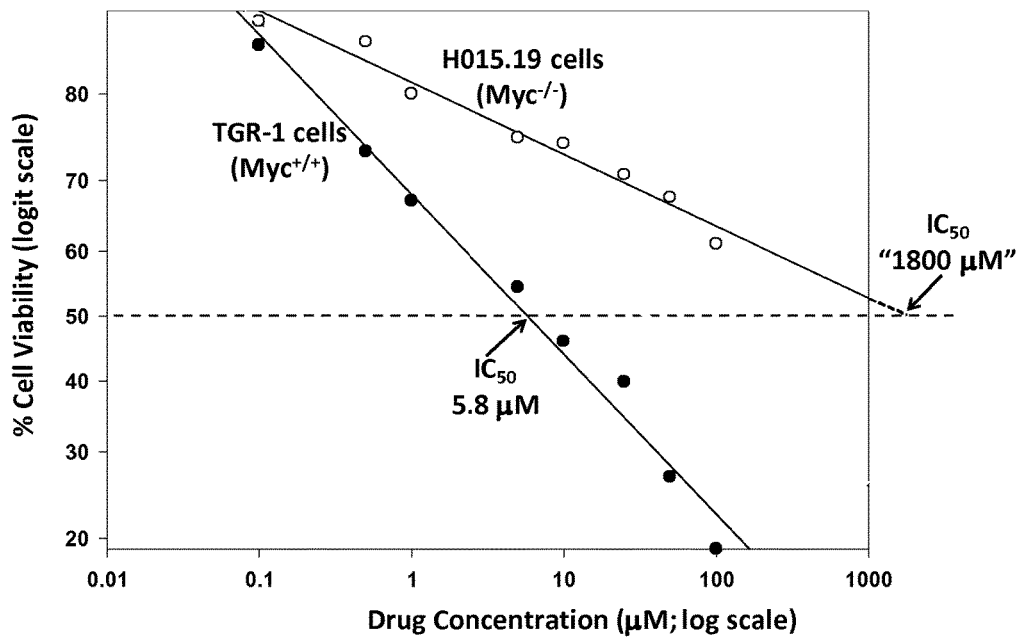
FIG. 1. Log it-plot for linear regression of cell viability data for the cell lines TGR-1 (Myc+/+) and H015.19 (Myc−/−) including the $IC_{50}$-values for the Amy22 compound in each cell line.

The TGR-1 and H015.19 cells were grown in DMEM supplemented with 10% FBS. Equal numbers of cells were seeded in multiple wells of 24-well plates at low density (<20% confluence at day 0), and either DMSO or DMSO-dissolved Amy22 (various concentrations) was added to the medium (final concentration of DMSO: 0.1%). Cell viability (sextuplicates) was measured on day 3 by using a standard MTT (Thiazolyl Blue Tetrazolium Bromide) colorimetric assay (Mosmann, 1983). Half-maximal inhibitory concentrations ($IC_{50}$) were determined using a log it-log plot and linear regression of the data (SigmaPlot software; Systat Software, Inc., San Jose, Calif., USA), as shown in FIG. 1 and Table 1. The measured data were plotted on the log it-log plot for linear regression of cell viability data (average values from 5 independent experiments in each case), in order to calculate the Amy22 $IC_{50}$ for the sibling cell lines that differ only in the presence or absence of Myc (TGR-1 and H015.19 cells, respectively). The $IC_{50}$ for H015.19 cells was calculated by extrapolation. The average values±S.E.M are shown in Table 1 below.

TABLE 1

Cell viability of TGR-1 and H015.19 cells after Amy22 administration

| Amy22 Concentration (μM) | TGR-1 Cells (%) | H015.19 Cells (%) |
|---|---|---|
| 0.1 | 84.4 ± 5.0 | 86.3 ± 5.9 |
| 0.5 | 73.7 ± 4.0 | 84.7 ± 5.7 |
| 1 | 67.3 ± 4.1 | 80.0 ± 4.1 |
| 5 | 54.5 ± 4.6 | 75.3 ± 8.8 |
| 10 | 46.0 ± 2.5 | 74.6 ± 4.9 |
| 25 | 39.9 ± 2.2 | 70.8 ± 5.1 |
| 50 | 26.8 ± 4.8 | 67.8 ± 4.0 |
| 100 | 19.0 ± 3.7 | 61.1 ± 3.8 |

The comparative $IC_{50}$ values of test compounds having the formulas (III) and (IV), respectively, were measured and determined as described by the above protocol:

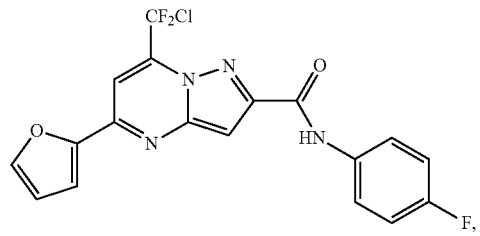

(III)

or formula (IV)

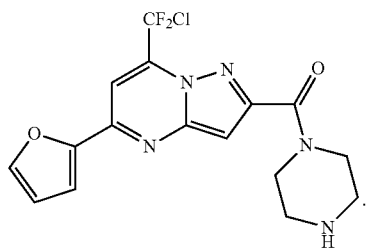

(IV)

The resulting $IC_{50}$ values are summarized in Table 2.

TABLE 2

Cell viability of TGR-1 and H015.19 after comparative compound administration

| Compound | TGR-1 Cells $IC_{50}$ (μM) | H015.19 Cells $IC_{50}$ (μM) |
|---|---|---|
| Amy22 | 5.8 | 1800 |
| formula (III) | 6.5 | 13.4 |
| formula (IV) | 12.3 | 58.8 |

Example 2: Efficacy of Amy22 Action on Cultured Mouse Pancreatic Cancer Cells

As already described in Stellas et al., JNCI 2014, the PdxCre; aKras* double transgenic mice are moribund at 30 days postpartum. At this age, mice were euthanized and their pancreatic tumors were excised and minced under sterile conditions in a Petri dish. The minced tissue was placed in a solution of trypsin/collagenese (1:1) for 30 minutes and fresh DMEM was then added to the Petri dish. The tissue was further dissociated into a single cell suspension using a 18G syringe. The tumor cells were cultured continuously until a homogeneous population appeared one month later. The cells were stored frozen in liquid nitrogen. The morphology and the cell cycle of the newly-established cell line remained stable after many passages.

Figure 2:
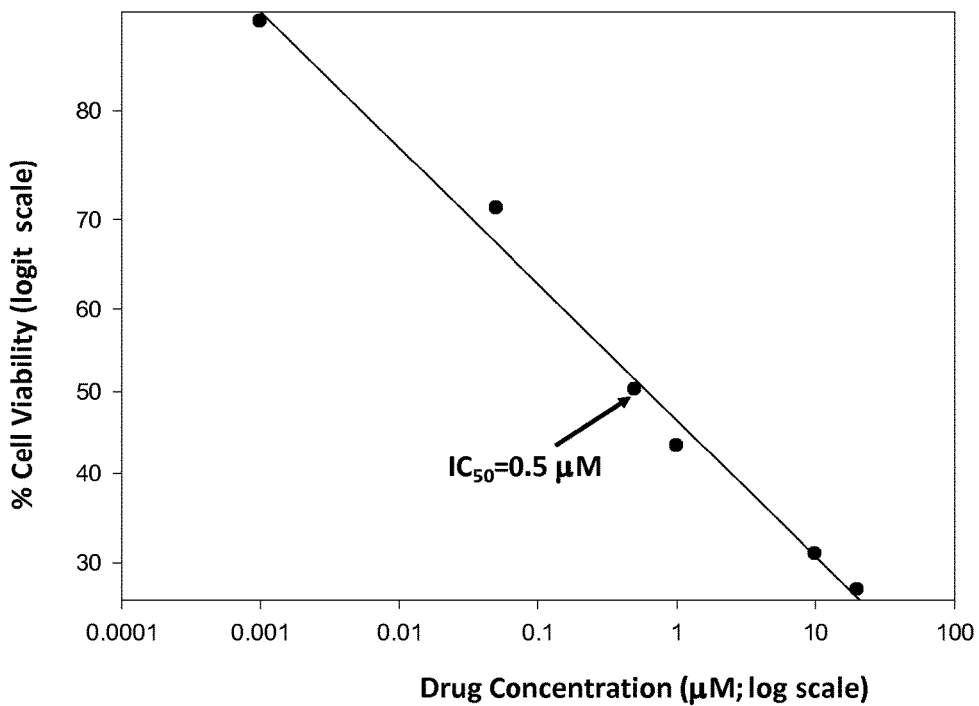
FIG. 2. Log it-log plot for linear regression of cell viability data for calculating the $IC_{50}$-values for the Amy22 compound for a cancer cell line derived from the Kras*-induced mouse pancreatic cancer.

The mouse pancreatic cancer cells were grown in DMEM supplemented with 10% FBS. Equal numbers of cells were seeded in multiple wells of 24-well plates at low density (<20% confluence at day 0), and either DMSO or DMSO-dissolved Amy22 (various concentrations) was added to the medium (final concentration of DMSO: 0.1%). Cell viability (sextuplicates) was measured on day 3 by using a standard MTT (Thiazolyl Blue Tetrazolium Bromide) colorimetric assay (Mosmann, 1983). Half-maximal inhibitory concentrations ($IC_{50}$) were determined using a log it-log plot and linear regression of the data (SigmaPlot software; Systat Software, Inc., San Jose, Calif., USA), as shown in FIG. 2. In order to calculate the Amy22 $IC_{50}$ in mouse pancreatic cancer cells, the measured values were plotted in the form of a log it-log plot for linear regression of cell viability data (a representative out of three independent experiments is shown).

Figure 3:
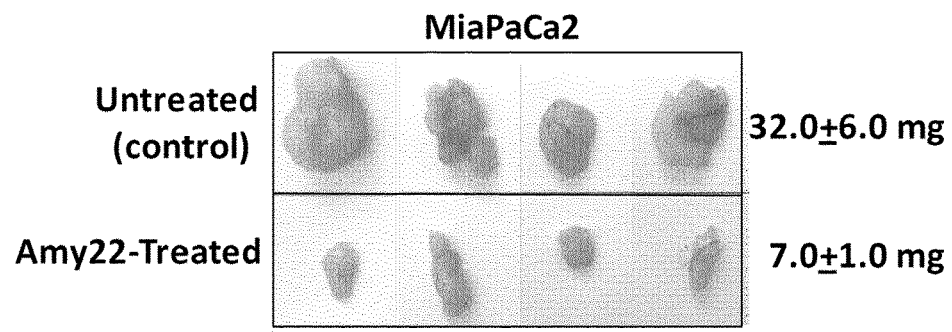
FIG. 3. Amy22 treatment of xenografts generated by heterotopic transplantation of the human pancreatic ductal adenocarcinoma cell line MiaPaCa2 or a mouse mammary carcinoma cell line generated from MMTV-Myc tumors.
Figure 3:
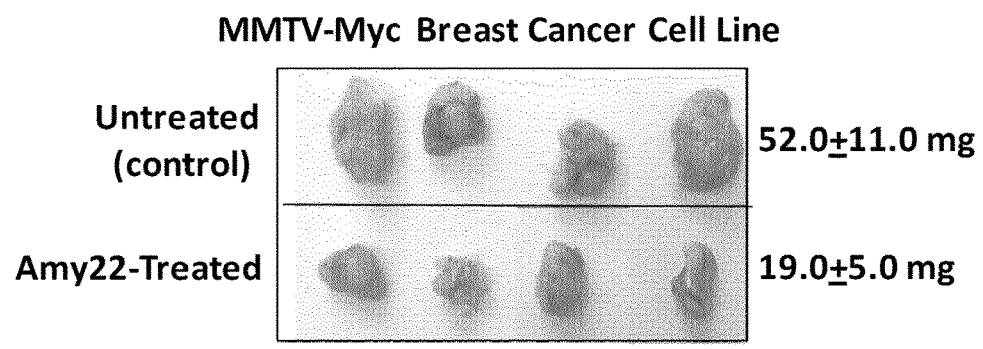

Example 3: Amy22 Treatment of Xenografts Generated by Heterotopic Transplantation of Human Pancreatic Ductal Adenocarcinoma Cell Line MiaPaCa2 or Mouse Mammary Carcinoma Cell Line MMTV-Myc For transplantation, eight-week old NOD/SCID mice were anesthetized using a steady flow of a mixture of isofluorane gas (4%) and oxygen and inoculated subcutaneously into their lateral flanks with $10^6$ cancer cells and monitored daily until the tumors became palpable (tumor volume ~100 $mm^3$). The mice were then divided randomly into two groups for Amy22 (150 mg/kg) or vehicle administration for a period of two weeks. Average weights±S.E.M (n=4 in each case) are indicated (p<0.001 and <0.05 for MiaPaCa2 and MMTV-Myc, respectively). Immunohistochemical analysis of the MiaPaCa2 xenografts using an antibody against the cell proliferation marker Ki67 showed reduced proliferation after treatment in comparison with the controls (proliferation index 15.0±3.3% and 69.9±5.1%, respectively). Amy22 also induced apoptosis. FIG. 3 illustrates the gross appearance of surgically recovered Amy22-treated or untreated (control) xenografts.

Example 4: Micro PET/CT Imaging of Pdx1-Cre/KRAS*A Mouse Treated With Amy22

Figure 4:
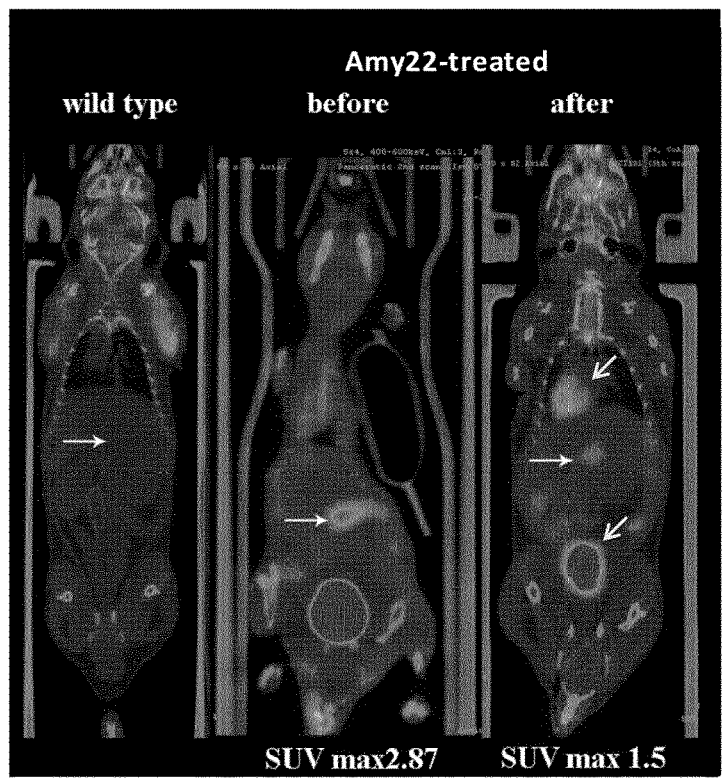
FIG. 4. Example of micro PET/CT imaging of Pdx1-Cre/KRAS*A mouse (compared with a negative wild-type control) at the beginning and end of treatment (one month) of pancreatic ductal adenocarcinoma (PDA) with the Amy22 compound.

PET/CT images were acquired of a Pdx1-Cre/KRAS*A mouse at the beginning and end of treatment (one month) of pancreatic ductal adenocarcinoma (PDA) with the Amy22 compound (cf. FIG. 4; a representative out of three independent experiments is shown). Dosing solutions of 20 mg/ml Amy22 in 0.5% carboxymethyl cellulose (CMC) were used for daily administration per os (0.15 ml per animal, dose 150 mg/kg) for 30 days. The diminished uptake of $^{18}$F-FDG by remnants of PDA is evident and measured by the standardized uptake values (SUV values) that were 2.87 at the beginning and 1.5 at the end of the treatment. The white arrows indicate the anatomical sites of pancreata. High-level concentration of $^{18}$F-FDG in the urinary bladder (excretion of the tracer) and also in the heart (yellow arrows) is noted. The treated mice are still alive 3 months post-treatment with no evident signs of cachexia.

Example 5: Micro PET/CT Imaging of Pdx1-Cre/KRAS*A Mouse Treated with Gemcitabine Alone or with and Combination of Gemcitabine and Amy22

Figure 5:
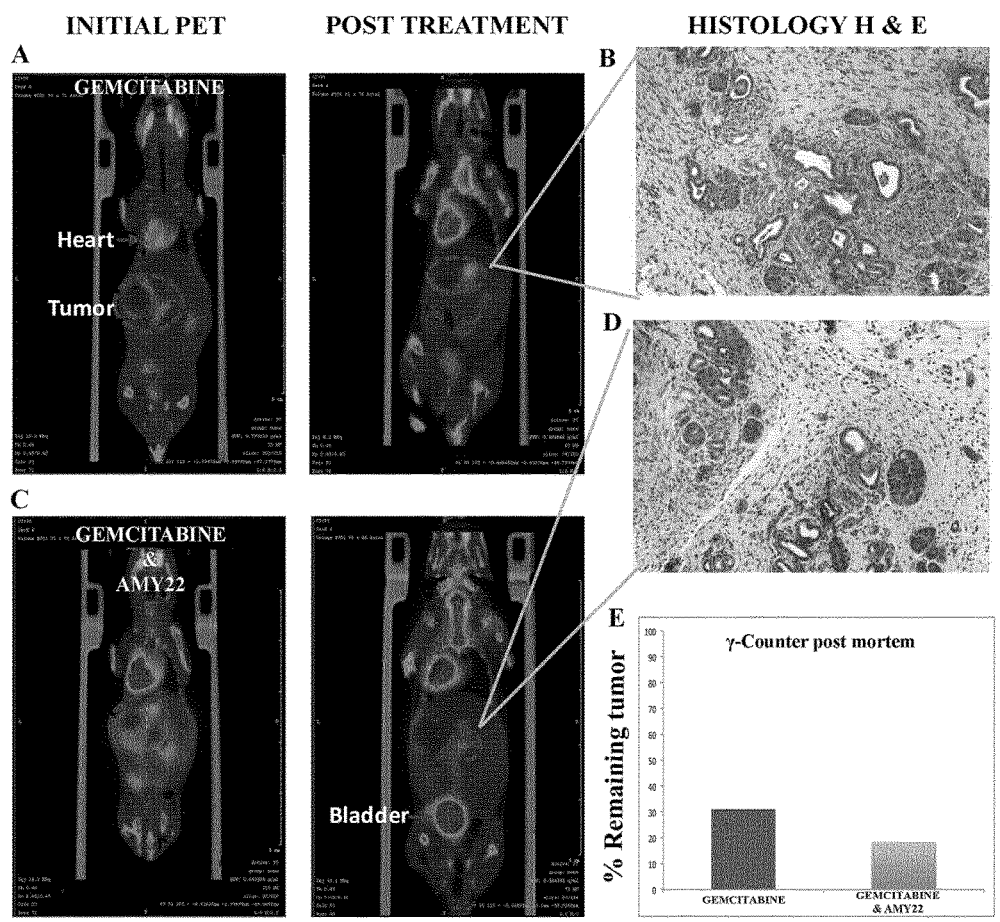
FIG. 5: Example of micro PET/CT imaging of Pdx1-Cre/KRAS*A mouse at the beginning and end of treatment (one month) of pancreatic ductal adenocarcinoma (PDA) with Gemcitabine alone, or with Gemcitabine and Amy22.

The representative PET/CT images shown were acquired for Pdx1-Cre/KRAS*A mice at the beginning and end of treatment (one month) of pancreatic ductal adenocarcinoma (PDA) using either Gemcitabine alone or a combination of Gemcitabine and Amy22. The scheme used for the treatment was as follows: weekly IP administration of Gemcitabine (300 mg/kg) in both cases and daily administration of AMY22 per os (150 mg/kg) in the combination treatment (cf. FIG. 5).
A: PET/CT of a mouse before and after treatment with Gemcitabine, as monotherapy). Shrinkage in tumor size and 18F-FDG uptake (dotted circles) is evident.
B: Histopathological features (H & E staining) of the treated tumor in (A). The analysis revealed the presence of scared fibrotic tissue and remnants of cancer cells. A few normal acini were also present.
C: PET/CT of a mouse before and after treatment with a combination of Gemcitabine and Amy22. The diminished uptake of $^{18}$F-FDG by remnants of PDA is evident (compare the size of dotted circles).
D: Histopathological features (H & E staining) of the treated tumor in (C). The analysis revealed the presence of scared fibrotic tissue, remnants of cancer cells and a larger area consisting of normal acini.
E: Gamma counting of the exact overall $^{18}$F-FDG uptake post-mortem reveals that the remaining tumor after treatment with Gemcitabine alone was 31% of that of untreated PDA tumors (not shown; see Stellas et al., JNCI, 2014). The corresponding percentage after the combination treatment was 18.6%.
In some scans, a high-level concentration of $^{18}$F-FDG in the urinary bladder (excretion of the tracer) could be observed. High uptake of radioactivity (unrelated to the presence of tumor) was also noted in the heart.
Accordingly, Amy22 enhanced the efficacy of Gemcitabine, which is classically used for human PDA chemotherapy.

Example 6: Micro PET/CT Imaging of Pdx1-Cre/KRAS*A Mouse Treated with Abraxane Alone or with a Combination of Abraxane and Amy22

The representative PET/CT images shown were acquired for Pdx1-Cre/KRAS*A mice at the beginning and end of treatment (one month) of pancreatic ductal adenocarcinoma (PDA) using either Abraxane alone or a combination of Abraxane and Amy22. (cf. FIG. 6). The dosing scheme used for the treatment was as follows: weekly IP administration of Abraxane (40 mg/kg) in both cases and daily administration of AMY22 per os (150 mg/kg) in the combination treatment (cf. FIG. 6).

PET/CT images were acquired of a representative Pdx1-Cre/KRAS*A mouse at the beginning and end of treatment (one month) of pancreatic ductal adenocarcinoma (PDA) with
A: PET/CT of a mouse before and after treatment with Abraxane, as monotherapy (representative pictures from treated cohort). Shrinkage in tumor size and $^{18}$F-FDG uptake (dotted circles) is evident.
B: Histopathological features (H & E staining) of the treated tumor in (A). The analysis revealed the presence of scared fibrotic tissue and remnants of cancer cells. A few normal acini were also present.
C: PET/CT of a mouse before and after treatment with a combination of Abraxane and Amy22 (representative pictures from treated cohort). The diminished uptake of $^{18}$F-FDG by remnants of PDA is evident (compare the size of dotted circles).
D: Histopathological features (H & E staining) of the treated tumor in (C). The analysis revealed the presence of scared fibrotic tissue, remnants of cancer cells and a larger area consisting of normal acini.
E: Gamma counting of the exact overall $^{18}$F-FDG uptake post-mortem reveals that the remaining tumor after treatment with Abraxane alone was 27% of that of untreated PDA tumors (not shown; see Stellas et al., 2014). The corresponding percentage after the combination treatment was 12.8%.

Amy22 thus enhanced the efficacy of Abraxane (which is currently the new gold standard of human PDA chemotherapy).

Example 7: Blood Concentrations of Amy22 Following Administration to Mice by Oral Gavage (140 mg/kg in 0.5% CMC)

Animals at the age of 10 weeks were fasted overnight and weighed before dosing (average weight=21.6 g, n=6 male C57BL/6N). Dosing solutions of 20 mg/ml Amy22 in 0.5% carboxymethyl cellulose (CMC) were used for administration per os (0.15 ml per animal, dose 140 mg/kg). A serial tail bleeding protocol was used for the collection of blood samples. Blood samples (10 µl) were collected at selected time points (0.5, 1, 2, 4, 8, 24 hours) in tubes containing 40 µl sodium citrate (0.1 M, pH 4.5) and stored at −80° C. until sample extraction. Samples were prepared for quantification by protein precipitation and evaporation. Amy22 was quantified by LC-MS/MS analysis. Results are summarized below.

Pharmacokinetic Parameters Using Non-Compartmental Analysis

| | |
|---|---|
| $C_{max}$ | 6.2 ± 1.1 µM |
| $t_{max}$ | 1.5 ± 0.5 hr |
| Elimination rate constant ($k_e$) | 0.2 ± 0.1 hr$^{-1}$ |
| $AUC_{0-24}$ | 33.6 ± 8.3 µM × hr |
| $AUC_{0-\infty}$ | 35.4 ± 9.5 µM × hr |

The data demonstrate that Amy22, when dosed orally at an efficacious dose, resulted in appreciable blood concentrations (>1 micro molar) up to at least 8 hr post dose.

Example 8: Synthesis Scheme for the Generation of the Compound of Formula (II)

Stage 1: Generation of Compound (3) by Reacting Compound (1) and (2)

| | Weight (g) | MW | Amount (mmol) | Eq. | density (g/cm³) | Vol. (mL) |
|---|---|---|---|---|---|---|
| 1 | 5.8 | 158.53 | 36.6 | 1.1 | 1.252 | 4.63 |
| 2 | 3.66 | 110.11 | 33.25 | 1 | | |
| LiHMDS | | | 39.9 | 1.2 | | |
| THF | 7 mL for solution of 1 | | | | | |
| | 15 mL for LiHMDS solution | | | | | |

Compounds 1 and 2 were dissolved in THF. Subsequently, LiHMDS was added dropwise. The reaction was carried out under Argon atmosphere at 0° C. for about 1 h after LiHMDS had been added. The solvent was evaporated and the reaction mixture was purified by adding a 1:1 mixture of EtOAc/6M aq.HCl, separating the aqueous phase, and subsequent washes of the organic phase 1:1 with H$_2$O and brine. Final traces of H$_2$O were removed with Na$_2$SO$_4$ and finally the organic solvent was removed by evaporation.

Stage 2a: Generation of (D1) by Reacting Compounds (5) and (3)

| | Weight (g) | MW | Amount (mmol) | Eq. |
|---|---|---|---|---|
| 5 | 3.3 | 127.10 | 24.4 (note 1) | 1 |
| 3 | 9.8 | 222.57 | 43.9 | 1.8 |
| HCl (2N) | 34 | | | |
| AcOH | 40 | | | |

Compounds 5 and 3 were dissolved in a solution of HCl and AcOH and reacted at 140° C. under reflux for 6 h, and subsequently at 25° C. for 16 h. During that time, an orange solid was formed and after the end of the reaction, the solid was removed by filtration. Subsequently, the solid was washed with ice-cold water, and then with EtOAc/Toluene 1:1. The filtrate was collected and the solvent was removed by rotary evaporation to obtain compound D1.

Stage 2b: Hydrolysis of Compound (6) to Obtain Compound (7)

| | Weight (g) | MW | Amount (mmol) | Eq. |
|---|---|---|---|---|
| 6 | 1.2 | 231.251 | 5.19 | 1 |
| NaOH (2N) | | 20 mL | | |
| EtOH | | 20 mL | | |

Compound 6 was dissolved in EtOH at 25° C. Subsequently, the 2N NaOH solution was added at 25° C. and the reaction mixture was stirred at 70° C. for 3 hours, then cooled down to 0° C. Upon adding HCl (50% (w/v) in water) to adjust to pH 1, a white precipitate was formed. The precipitate was filtrated and dry precipitated in a water aspirator. An azeotrope consisting of EtOH, Et$_2$O and benzene was added, followed by drying in high vacuum to obtain compound (7).

Stage 3: Generation of Amy22 (D5) by Reacting Compound (D1) and Compound (7)

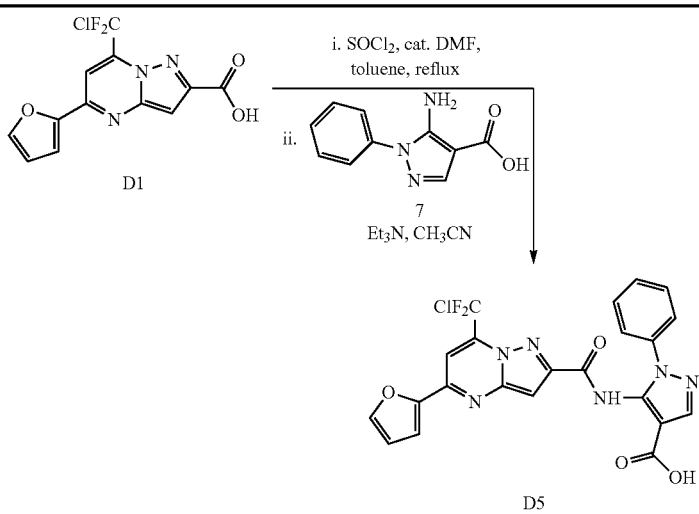

| | Weight (g) | MW | Amount (mmol) | Eq | density (g/cm$^3$) | Vol. (mL) |
|---|---|---|---|---|---|---|
| Step (i) | | | | | | |
| D1 | 1.6 | 313.64 | 5.1 | 1 | | |
| SOCl$_2$ | 4.92 | 118.97 | 41.3 | 8 | 1.64 | 3.0 |
| DMF | 0.037 | 73.09 | 0.51 | 0.1 | 0.948 | 0.039 |
| Toluene | 25 mL | | | | | |
| Step (ii) | | | | | | |
| 7 | 0.83 | 203.20 | 4.08 | 0.8 | | |
| Et$_3$N | 2.58 | 101.19 | 25.5 | 5 | 0.726 | 3.55 |
| CH$_3$CN | 20 mL | | | | | |

Step i: D1 was dissolved in toluene under argon atmosphere at 25° C. SOCl$_2$ and DMF were added and the reaction mixture was stirred under reflux at 120° C. for 6 h. Subsequently, the reaction mixture was cooled to 25° C. and solvent removed under vacuum. SOCl$_2$ and HCl were removed under high vacuum.

Step ii: Subsequently, CH$_3$CN was added at 25° C. under inert argon atmosphere. Then, Et$_3$N and the amino acid 7 were added to the reaction mixture, and the mixture was stirred for 48 h at 25° C. under argon atmosphere. Water (100 mL) was added and the reaction mixture was stirred for further 15 minutes at 25° C. EtOAc (200 mL) was subsequently added, and the aqueous and the organic phase were separated. The organic phase was washed with brine and the remaining water in the organic phase was removed by Na$_2$SO$_4$. Finally, the organic solvent was removed under vacuum. Amy22 (D5) was then purified by flash chromatography using CHCl$_3$/MeOH (95:5-8:2) to remove the amino acid 7. Finally, CHCl$_3$/MeOH was removed under vacuum to obtain Amy22 (D5, 1.2 g (51%)) as a yellow solid in purified form.

REFERENCES de Alboran, I. M. et al. Analysis of C-MYC function in normal cells via conditional gene-targeted mutation. *Immunity* 14, 45-55 (2001).

Berg, T., et al., Small-molecule antagonists of Myc Max dimerization inhibit Myc-induced transformation of chicken embryo fibroblasts, *Proc Natl Acad Sci USA* 99, 3830-3835 (2002).

Boulware, S. B. et al., Triplex-forming oligonucleotides targeting c-Myc potentiate the antitumor activity of gemcitabine in a mouse model of human cancer. *Mol. Carcinogen. in press* (2013).

D'Agnano, I. et al., Oligopeptides Impairing the Myc-Max Heterodimerization Inhibit Lung Cancer Cell Proliferation by Reducing Myc Transcriptional Activity. *J Cell Physiol* 210, 72-80 (2007).

Gomez-Curet, I., et al., c-Myc inhibition negatively impacts lymphoma growth. *J Pediatr Surg* 41, 207-211 (2006).

Guo, J., et al. Efficacy, pharmacokinetics, tissue distribution, and metabolism of the Myc-Max disruptor, 10058-F4 [Z,E]-5-[4-ethylbenzylidine]-2-thioxothiazolidin-4-one, in mice. *Cancer Chemother Pharmacol* 63, 615-625 (2009).

Huanga, M J., A small-molecule c-Myc inhibitor, 10058-F4, induces cell-cycle arrest, apoptosis, and myeloid differentiation of human acute myeloid leukemia, *Exp Hematol* 34, 1480-1489 (2006).

Kiessling, A., et al., Selective Inhibition of c-Myc/Max Dimerization by a PyrazoloA[1,5-a]-pyrimidine. *Chem Med Chem* 2, 627-630 (2007).

Lin C P et al., Small-molecule c-Myc inhibitor, 10058-F4, inhibits proliferation, downregulates human telomerase reverse transcriptase and enhances chemosensitivity in human hepatocellular carcinoma cells, *Anticancer Drugs*, 18, 161-70 (2007).

McGrath J. P. et al., Structure and organization of the human Ki-ras proto-oncogene and a related processed pseudogene, Nature 304, 501-506 (1983).

Mateyak M K, Obaya A J, Adachi S, Sedivy J M. Phenotypes of c-Myc-deficient rat fibroblasts isolated by targeted homologous recombination. Cell Growth Differ 1997; 8(10):1039-1048.

Mosmann, T. Rapid colorimetric assay for cellular growth and survival: application to proliferation and cytotoxicity assays. J Immunol Methods 65, 55-63 (1983).

Sampson V B, et al., MicroRNA let-7a down-regulates MYC and reverts MYC-induced growth in Burkitt lymphoma cells, Cancer Res 67, 9762-70 (2007).

Soucek, L., et al. Modelling Myc inhibition as a cancer therapy. Nature 455, 679-683 (2008).

Stellas D., et al., Therapeutic effects of an anti-Myc drug on mouse pancreatic cancer, J. Natl Cancer Inst. 106 (2014)

Stewart, T. A., Pattengale, P. K. & Leder, P. (1984). Spontaneous mammary adenocarcinomas in transgenic mice that carry and express MTV/myc fusion genes. Cell 38, 627-637.

Vita, M. & Henriksson, M. The Myc oncoprotein as a therapeutic target for human cancer. Semin Cancer Biol 16, 318-330 (2006)

Watson J. Oxidants, antioxidants and the current incurability of metastatic cancers. Open Biol 3, 120144 (2013).

Xu Y., et al., A credit-card library approach for disrupting protein-protein interactions, *Bioorg Med Chem* 14, 2660-2673 (2006).

Yamada H, et al., Amplifications of both c-Ki-ras with a point mutation and c-myc in a primary pancreatic cancer and its metastatic tumors in lymph nodes. *Jpn J Cancer Res.* 77, 370-375 (1986).

Yin X., Low molecular weight inhibitors of Myc-Max interaction and function. *Oncogene* 22, 6151-6159, (2003).

n is 0;

X is N;

$CY_3$ is $CF_3$, $CF_2Cl$, or $CFCl_2$;

$R_1$ is

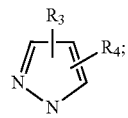

$R_2$ is 2-thiophenyl, 2-furanyl, 2-pyrrolyl, or 5-pyrazolyl;

$R_3$ is a group —$R_5$—COOH group or a pharmaceutically acceptable salt thereof; wherein $R_5$ is either a bond or a $C_1$-alkyl group; and $R_4$ is selected from any one of the following: substituted or unsubstituted cyclohexyl, substituted or unsubstituted tetrahydropyran, piperidine, thiacyclohexane, dioxane, piperazine, morpholine, pyran, oxazine, thiazine, substituted or unsubstituted phenyl, pyridine, or pyrimidine.

2. The compound of claim 1, wherein $R_2$ is 2-furanyl; and $R_3$ is a carboxyl group directly attached to the pyrazole ring, or a pharmaceutically acceptable salt thereof; and $R_4$ is a phenyl group.

3. The compound of claim 1, having the following formula (II):

---

---

The invention claimed is:

1. A compound of formula (I)

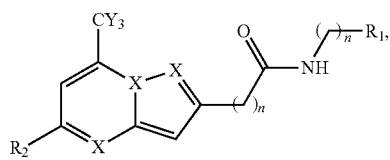

or a tautomer, polymorph, metabolite, or a pharmaceutically acceptable salt thereof, wherein

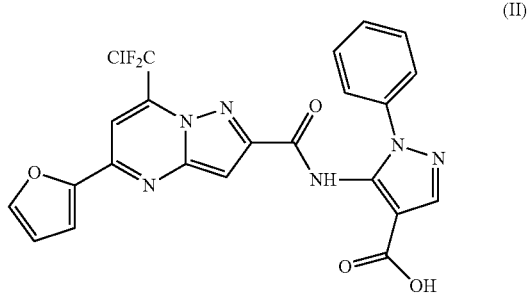

or a pharmaceutically acceptable salt thereof.

4. A pharmaceutical composition comprising the compound of claim 1, optionally further comprising one or more additional therapeutic agents.

5. The pharmaceutical composition of claim 4, wherein the one or more additional therapeutic agents are selected from the group consisting of:

10-Hydroxycamptothecin, 17-Allylamino-geldanamycin, 2-Methoxyanti-mycin A3, 3,4-Dichloroisocoumarin, 4-Hydroxyphenylretinamide, 9-cis Retinoic acid, Abiraterone, Ado-Trastuzumab Emtansine, Adriamycin, Afatinib, N-(3-chlorophenyl)-6,7-dimethoxyquinazolin-4-amine, 2-Amino-4-(1H-indol-5-yl)-1,1,3-tricyanobuta-1,3-diene, Aldesleukin, Alemtuzumab, Amifostine, Anastrozole, Anisomycin, Aphidicolin, Arsenic Trioxide, Asparaginase *Erwinia chrysanthemi*, Axitinib, N-[2(S)-(2(R)-2-Amino-3-mercaptopropylamino)-3-methylbutyl]-L-phenylalanyl-L-methionine trifluoroacetate salt, Bacillus Calmette-Guerin, bisphenol A diglycidyl ether, Bendamustine, Beta-lapachone, Betulinic acid, Bevacizumab, Bexarotene, Bicalutamide, BisBenzimide, Bleomycin, Bortezomib, Bosutinib, Buserelin, Busulfan, Cabazitaxel, Calpeptin, Camptothecin, Caffeic acid phenethyl ester, Capecitabine, Carboplatin, Carboplatin, Carfilzomib, Carmustine, Cetuximab, Chlorambucil, Ciglitazone, Cisplatin, Clodronate, Clofarabine, Crizotinib, Curcumin, Cyclo[Arg-Gly-Asp-D-Phe-Val], Cycloheximide, Cyclopamine, Cyclophosphamide, Cyclosporin A, Cyproterone, Cytarabine, D12-Prostaglandin J2, Dabrafenib, Dacarbazine, Dactinomycin, Dasatinib, Daunorubicin, Degarelix, Denosumab, Dexamethasone, Docetaxel, Doxorubicin, Ebselen, Ellipticine, Enzalutamide, Epirubicin, Erlotinib, Etoposide, Everolimus, Exemestane, Fludarabine, Fluorouracil, Flutamide, Folinic acid, Fulvestrant, Gefitinib, Geldanamycin, Gemcitabine, Genistein, Gingerol, Gliotoxin, Goserelin, 2-Chloro-5-nitrobenzanilide, 2-Amino-6-bromo-α-cyano-3-(ethoxycarbonyl)-4H-1-benzopyran-4-acetic acid ethyl ester, Hinokitiol, Sobuzoxane, Idarubicin, ifosfamide, Imatinib, Indomethacin, Ipilimumab, Irinotecan, Ixabepilone, Lanreotide, Lapatinib, Lenalidomide, Letrozole, Leucovorin, Leuprolide, Medroxyprogesterone, Megestrol, Melphalan, Mepesuccinate, Mercaptopurine, Mesna, Methotrexate, Methoxy verapamil, carbobenzoxy-L-leucyl-L-leucyl-L-leucinal, Mitomycin C, Mitoxantrone, N,N-Dimethylsphingosine, Nelarabine, Nilotinib, Octreotide, Ofatumumab, Oligomycin A, Omacetaxine, Oxaliplatin, Paclitaxel, Pamidronate, Panitumumab, Pazopanib, Pegaspargase, Pemetrexed, Pertuzumab, Pifithrin, plerixafor, Podophyllotoxin, Pomalidomide, Ponatinib, Prednisone, 2,2-Bis(hydroxymethyl)-1-azabicyclo[2.2.2]octan-3-one, Procarbazine, Radium 223 Dichloride, Raltitrexed, Rapamycin, Recombinant Human Papillomavirus (HPV) Bivalent Vaccine, Recombinant HPV Quadravalent Vaccine, Recombinant HPV Bivalent Vaccine, Recombinant HPV Quadravalent Vaccine, Recombinant Interferon Alfa-2b, Regorafenib, Resveratrol, all trans Retinoic acid, Rheumatrex, Rituximab, Rolipram, Roscovitine, Rottlerin, Shikonin, Sipuleucel-T, Sirolimus, Sorafenib, Sphingosine, Splitomycin, Staurosporine, Stilboestrol, Streptozocin, 3-(4-Dimethylaminobenzylidenyl)-2-indolinone, 3-[[(4-Dimethyl-amino)phenyl] methylene]-1,3-dihydro-2H-indol-2-one, Sulindac sulphide, Sunitinib, Tamoxifen, Temozolomide, Temsirolimus, Thalidomide, Topotecan, Toremifene, Trametinib, Trastuzumab, Trichostatin-A, Trifluoperazine, 4-[(E)-2-(5,6,7,8-Tetrahydro-5,5,8,8-tetramethyl-2-naphthalenyl)-1-propenyl]benzoic acid, 3,4-Dihydroxy-α-cyanothiocinnam-amide, (3-Hydroxy-4-nitrobenzylidene)malononitrile, Valproic acid, Vemurafenib, Verapamil, Vinblastine, Vincristine, Vinorelbine, Wortmannin, 4-Chloro-6-(2,3-xylidino)-2-pyrimidinylthioacetic acid, Ziv-Aflibercept, Zoledronic Acid, salts thereof, and combinations thereof.

6. The pharmaceutical composition of claim 4, further comprising one or more additional therapeutic agents, which are selected from the group consisting of Acetylsalicylic acid, Diflunisal, Salsalate, Ibuprofen, Dexibuprofen, Naproxen, Fenoprofen, Ketoprofen, Dexketoprofen, Flurbiprofen, Oxaprozin, Loxoprofen, Indomethacin, Tolmetin, Sulindac, Etodolac, Ketorolac, Diclofenac, Nabumetone, Piroxicam, Meloxicam, Tenoxicam, Droxicam, Lornoxicam, Isoxicam, Mefenamic acid, Meclofenamic acid, Flufenamic acid, Tolfenamic acid, Celecoxib, Rofecoxib, Valdecosib, Parecoxib, Lumiracoxib, Etoricoxib, Firocoxib, Nimesulide, Licofelone, H-harpagide, Lysine clonixinate, pharmaceutically acceptable salts thereof, and combinations thereof.

7. The pharmaceutical composition of claim 4, further comprising one or more agents inducing unscheduled DNA repair synthesis (UDS) at a target oncogene, and, optionally, one or more antimetabolites.

8. The pharmaceutical composition of claim 7, wherein the agent inducing unscheduled DNA repair synthesis (UDS) is a triple helix forming oligonucleotide specifically binding to Myc; and/or
wherein the antimetabolite is a purine or pyrimidine analog.

9. A method of treating a cancerous disease in a mammal, comprising the administration of a therapeutically effective amount to the mammal of the compound of claim 1.

10. The method of claim 9, wherein the mammal is human.

11. The method of claim 9, wherein the cancerous disease is susceptible to Myc overexpression and/or deregulation.

12. The method of claim 9, wherein the cancerous disease is selected from the group consisting of acute monocytic leukemia, acute myelogenous leukemia, acute myelomonocytic leukemia, acute promyelocytic leukemia, adult T-cell leukemia, adult T-cell lymphoma, astrocytoma, atypical carcinoid lung cancer, basal cell carcinoma, B-acute lymphocytic leukemia, B-cell acute lymphoblastic leukemia/lymphoma, Bladder cancer, brain cancer, breast cancer, bronchial cancer, Burkitt's lymphoma, cancer of the bile duct, cancer of unknown primary origin, cervix cancer, chronic myeloproliferative disorder, colon cancer, diffuse large cell lymphoma, endometrial cancer, ependymoma, esophageal cancer, gastric cancer, glioma, glioblastoma, head and neck cancer, hemagiopericytoma, hepatocellular carcinoma, Hodgkin's lymphoma, Kaposi's sarcoma, kidney cancer, large cell neuroendocrine carcinoma, large granular lymphocytic leukemia, leukemia, liver cancer, lung cancer, lymphoma, medulloblastoma, melanoma, Multiple myeloma, myelodysplastic syndrome, nasopharygeal cancer, neuroblastoma, NK cell tumor, non-Hodgkin's lymphoma, oesophageal squamous cell carcinoma, osteosarcoma, ovarian cancer, pancreatic cancer, peripheral T-cell leukemia, primary plasma cell leukemia, prostate cancer, renal clear cell carcinoma, retinoblastoma, rhabdomyosarcoma, sarcoma, small cell lung carcinoma, T-cell acute lymphoblastic leukemia, T-cell acute lymphoblastic lymphoma, testicular cancer, thymoma, urachal cancer, uterine cancer, vaginal cancer, and combinations thereof.

13. The method of claim 9, wherein the cancerous disease is selected from the group consisting of colon adenocarcinoma, lung adenocarcinoma, prostatic adenocarcinoma, urachal adenocarcinoma, vaginal adenocarcinoma, mammary adenocarcinoma, esophageal adenocarcinoma, bronchial adenocarcinoma, pancreatic adenocarcinoma, gastrointestinal adenocarcinoma; and combinations thereof.

14. A method for the manufacture of a compound of formula (I)

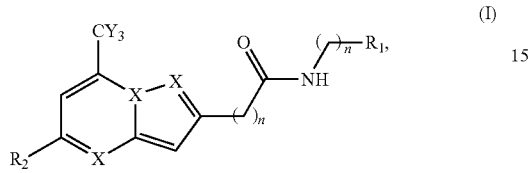
(I)

wherein the method comprises reacting a 2-carboxyl-substituted bicyclic moiety of formula (III):

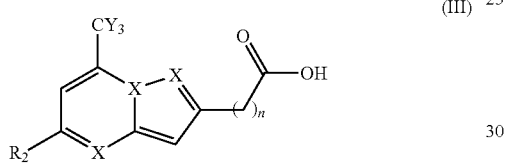
(III)

wherein X, $R_2$, $CY_3$ and n are defined as in claim 1, with a moiety $R_1$ as defined in claim 1 but with an additional amino-group to form the corresponding amide compound of formula (I) and, optionally, converting it to its corresponding pharmaceutically acceptable salt form.

15. The pharmaceutical composition of claim 5, wherein the one or more additional therapeutic agents are selected from the group consisting of:
Abiraterone, Ado-Trastuzumab Emtansine, Afatinib, Anastrozole, Bevacizumab, Cabazitaxel, Capecitabine, Carboplatin, Cisplatin, Crizotinib, Cyclophosphamide, Degarelix, Denosumab, Docetaxel, Doxorubicin, Enzalutamide, Epirubicin, Erlotinib, Etoposide, Everolimus, Exemestane, Fluorouracil, Fulvestrant, Gefitinib, Gemcitabine, Ixabepilone, Lapatinib, Letrozole, Leuprolide, Megestrol, Methotrexate, Mitomycin C, Paclitaxel, Pamidronate, Pemetrexed, Pertuzumab, Prednisone, Radium 223 Dichloride, Sipuleucel-T, Sunitinib, Tamoxifen, Topotecan, Toremifene, Trastuzumab, salts thereof, and any combination thereof.

16. The pharmaceutical composition of claim 6, further comprising one or more additional therapeutic agents, which are selected from the group consisting of Celecoxib, Rofecoxib, Valdecosib, Parecoxib, Lumiracoxib, Etoricoxib, Firocoxib, pharmaceutically acceptable salts thereof, and combinations thereof.

17. The pharmaceutical composition of claim 8, wherein the triple helix forming oligonucleotide has the sequence 3'-TGGGTGGGTGGT TTGTTTTTGGG-5' (SEQ ID NO:1, "Myc2T"); and/or
wherein the antimetabolite is selected from 5-fluorouracil, floxuridine, gemcitabine, cytarabine, 6-azauracil, and wherein the triple helix forming oligonucleotide has the sequence 3'-TGGGTGGGTGGT TTGTTTTTGGG-5', (SEQ ID NO:1, "Myc2T").

18. The method of claim 14, wherein the method is for preparing a compound of formula (II), or its pharmaceutically acceptable salt, by reacting a compound of formula (D1)

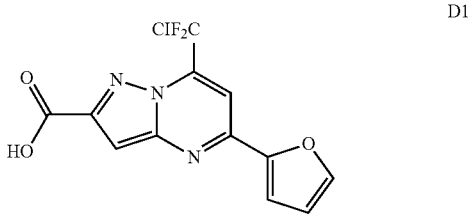
D1 with a compound of formula (7)

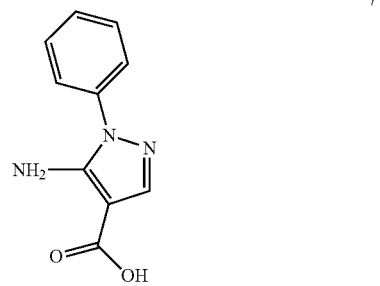
7 to yield the compound of formula (II):

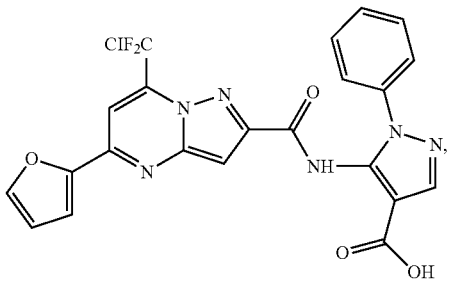

and, optionally, converting it to its corresponding pharmaceutically acceptable salt form.

* * * * *